United States Patent
Sasabe et al.

(10) Patent No.: US 12,096,689 B2
(45) Date of Patent: Sep. 17, 2024

(54) COMPOUND HAVING NITROGEN-CONTAINING SIX-MEMBERED AROMATIC RING STRUCTURE, AND MATERIAL FOR ORGANIC LIGHT-EMITTING-DIODE, ELECTRON TRANSPORT MATERIAL, AND ORGANIC LIGHT-EMITTING-DIODE USING THE SAME

(71) Applicant: FLASK Corporation, Yonezawa (JP)

(72) Inventors: Hisahiro Sasabe, Yonezawa (JP); Junji Kido, Yonezawa (JP); Tomohiro Maruyama, Yonezawa (JP); Tsukasa Owada, Yonezawa (JP); Tomoya Kawano, Yonezawa (JP); Yu Saito, Yonezawa (JP)

(73) Assignee: FLASK CORPORATION, Yonezawa (JP)

( * ) Notice: Subject to any disclaimer, the term of this patent is extended or adjusted under 35 U.S.C. 154(b) by 761 days.

(21) Appl. No.: 17/184,811

(22) Filed: Feb. 25, 2021

(65) Prior Publication Data

US 2021/0296596 A1 Sep. 23, 2021

(30) Foreign Application Priority Data

Mar. 12, 2020 (JP) .................................. 2020-042607
Feb. 2, 2021 (JP) .................................. 2021-014885

(51) Int. Cl.
*H01L 51/50* (2006.01)
*C07D 401/14* (2006.01)
(Continued)

(52) U.S. Cl.
CPC ....... *H10K 85/6576* (2023.02); *C07D 401/14* (2013.01); *C07D 409/14* (2013.01);
(Continued)

(58) Field of Classification Search
None
See application file for complete search history.

(56) References Cited

U.S. PATENT DOCUMENTS

2009/0072715 A1* 3/2009 Suzuri ................. H10K 50/165
313/504
2017/0092870 A1* 3/2017 Kim ...................... H10K 85/615

FOREIGN PATENT DOCUMENTS

JP 2008071993 A 3/2008
WO 2009107651 A1 9/2009
(Continued)

*Primary Examiner* — Gregory D Clark
(74) *Attorney, Agent, or Firm* — BUCHANAN, INGERSOLL & ROONEY PC

(57) ABSTRACT

Provided are a compound having the nitrogen-containing six-membered aromatic ring structure with high electron transport characteristic and high thermal stability, thereof electron transport material, and an OLED using the same. That is to say, a compound having the nitrogen-containing six-membered aromatic ring structure substituted by at least three nitrogen-containing six-membered aromatic groups, and an OLED material and an electron transport material comprising the compound having the nitrogen-containing six-membered aromatic ring structure. An OLED having a pair of anode and cathode and at least one organic layer including a light-emitting layer between the pair of the electrodes, wherein any of the organic layers comprises the compound having the nitrogen-containing six-membered aromatic ring structure. The compound having the nitrogen-containing six-membered aromatic ring structure according to this invention excellent in electron transport characteristic and thermal stability is suitable for an OLED material, especially an electron transport material.

16 Claims, 2 Drawing Sheets

(51) Int. Cl.
    *C07D 409/14*     (2006.01)
    *C09K 11/06*     (2006.01)
    *H10K 85/60*     (2023.01)
    *H10K 50/15*     (2023.01)

(52) U.S. Cl.
    CPC ............ *C09K 11/06* (2013.01); *H10K 85/654* (2023.02); *C09K 2211/1018* (2013.01); *H10K 50/15* (2023.02)

(56) References Cited

FOREIGN PATENT DOCUMENTS

| | | | |
|---|---|---|---|
| WO | 2013141097 | A1 | 9/2013 |
| WO | 2016089165 | A2 | 6/2016 |

\* cited by examiner

COMPOUND HAVING NITROGEN-CONTAINING SIX-MEMBERED AROMATIC RING STRUCTURE, AND MATERIAL FOR ORGANIC LIGHT-EMITTING-DIODE, ELECTRON TRANSPORT MATERIAL, AND ORGANIC LIGHT-EMITTING-DIODE USING THE SAME

BACKGROUND OF THE INVENTION

Field of the Invention

The present invention relates to a compound having nitrogen-containing six-membered aromatic ring structure, which is excellent in electron transport characteristic, and an organic light-emitting-diode using the same.

Description of the Related Art

An organic light-emitting-diode (OLED) is expected as the next generation flat panel displays (FPDs) and is applied to mobile phone displays, lighting, TV sets (television receivers) and so on, and further developments aiming at improvement of functions are continuously pursued. The organic light-emitting-diode is composed of a light-emitting layer, and a pair of electrodes facing each other with the light-emitting layer interposed. When an electric field is applied between the electrodes, electrons from a cathode and holes from an anode are injected into the light-emitting layer, and the electrons and the holes are recombined to form an excited state and emit energy as light when the excited state returns to a ground state.

Compared with inorganic light-emitting-diodes, a conventional organic light-emitting-diode has higher driving voltage and lower luminous efficiency, and because of heat generation of the device itself at the time of driving or its ambient temperature, the luminance may deteriorate due to a morphological change of its constituent materials. Therefore, researches have been continuously carried out for lowering voltage and improving efficiency.

First of all, it is necessary to reduce the driving voltage of the organic light-emitting-diode in order to put it to practical use. Reducing the driving voltage will lead to the improvement of the power efficiency, while energy barriers between OLED electrodes and organic layers may cause the voltage to increase and the efficiency to decrease. If the energy barrier between a cathode and an electron transport material is reduced, the driving voltage of the elemental device will be drastically lowered. Accordingly, researches are carried out on a new electron transport material capable of reducing the energy barrier between the cathode and the electron transport material.

To lower the driving voltage of the OLED material, the following compounds are reported: the compound substituted by triphenylenyl group and electron-withdrawing terpyridyl group through a pyridine ring (WO 2016/089165 A), and the compound substituted by three bipyridyl groups through a pyridine ring and the compound substituted by three bipyridyl groups through a pyrimidine ring, as compounds having high electron mobility and excellent hole blocking characteristic (WO 2009/107651 A). According to WO 2013/141097 A, the transparent electrode is composed of a conductive layer and an interlayer disposed adjacent to the conductive layer, wherein the interlayer includes a bipyridine derivative. The OLED equipped with such a transparent electrode shows both sufficient conductivity and high light transmittance. JP 2008-071993 A discloses the light-emitting-diode with low driving voltage and long lifetime, wherein the compound having a pyridine ring substituted by three diphenylpyridyl groups is used as a dopant in the light-emitting layer.

However, the nitrogen-containing heterocyclic compounds, as described above, become unstable as soon as they get holes and are easily deteriorated. If such compounds are used as an electron transport layer adjacent to a light-emitting layer, durability of the OLED may be reduced. When a hole blocking layer is composed of the nitrogen-containing heterocyclic compound, and an amine compound is used as a dopant in a light-emitting layer, the light-emitting layer works as a hole trap. Consequently, the device characteristics may be deteriorated due to the interaction between holes and the nitrogen-containing heterocyclic compound composing the hole blocking layer.

BRIEF SUMMARY OF THE INVENTION

In response to the above issue, an object of the present invention is to provide an electron transport material for organic light-emitting-diode with improved voltage and durability.

The present invention contains the items below.

The compound having the nitrogen-containing six-membered aromatic ring structure according to the present invention is substituted by at least three nitrogen-containing six-membered aromatic groups.

The compound having the nitrogen-containing six-membered aromatic ring structure according to the present invention is represented by the following general formula (1).

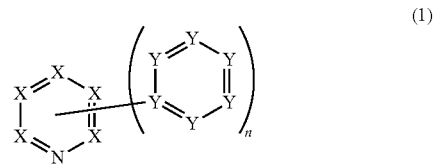

In the general formula (1), X and Y are carbon atoms substituted by R (—CR—) or nitrogen atoms. At least one of Ys is nitrogen atom; R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5. Six-membered rings formed by Ys may be the same or different each.

The compound having the nitrogen-containing six-membered aromatic ring structure according to the present invention is substituted by at least three substituted or unsubstituted pyridine groups.

The compound having the nitrogen-containing six-membered aromatic ring structure according to the present invention is represented by the following general formula (2).

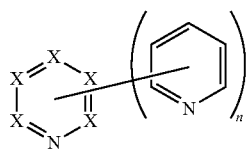

(2)

In the general formula (2), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5. The binding site for pyridyl group may be the same or different.

The compound having the nitrogen-containing six-membered aromatic ring structure according to the present invention is represented by the following general formula (3).

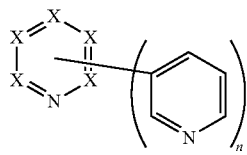

(3)

In the general formula (3), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5.

The compound having the nitrogen-containing six-membered aromatic ring structure according to the present invention is represented by the following general formula (4).

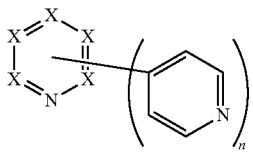

(4)

In the general formula (4), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5.

The compound having the nitrogen-containing six-membered aromatic ring structure according to the present invention is represented by the following general formula (5).

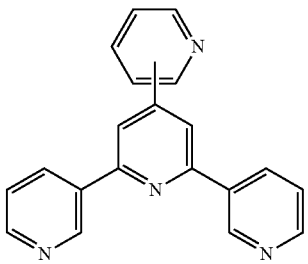

(5)

In the general formula (5), all or part of hydrogen atoms constituting the nitrogen-containing six-membered aromatic ring structure are substituted by an aryl group having 6 to 16 core carbon atoms.

The compound having the nitrogen-containing six-membered aromatic ring structure according to the present invention is represented by the following general formula (6).

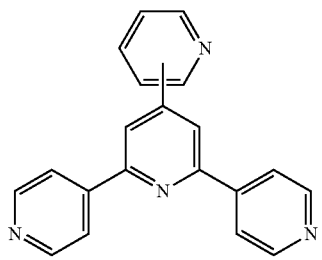

(6)

In the general formula (6), in one embodiment, all or part of hydrogen atoms constituting the nitrogen-containing six-membered aromatic ring structure are substituted by an aryl group having 10 to 18 core carbon atoms. In another embodiment, all or part of hydrogen atoms constituting the nitrogen-containing six-membered aromatic ring structure are substituted by an aryl group having 6 to 18 core carbon atoms.

The material for organic light-emitting-diode according to the present invention includes the compound having the nitrogen-containing six-membered aromatic ring structure.

The electron transport material for organic light-emitting-diode according to the present invention includes the compound having the nitrogen-containing six-membered aromatic ring structure.

The organic light-emitting-diode according to the present invention has a pair of anode and cathode electrodes, and at least one organic layer including a light-emitting layer between the pair of the electrodes, wherein any of the organic layers comprises the compound having the nitrogen-containing six-membered aromatic ring structure.

In the organic light-emitting-diode according to the present invention, any of the organic layers between the light-emitting layer and the cathode comprises the compound having the nitrogen-containing six-membered aromatic ring structure.

The compound having the nitrogen-containing six-membered aromatic ring structure according to the present invention has high electron transport characteristic and high thermal stability, which are suitable for a material for organic light-emitting-diode, especially, an electron transport material.

DESCRIPTION OF THE PREFERRED EMBODIMENTS

Figure 1:
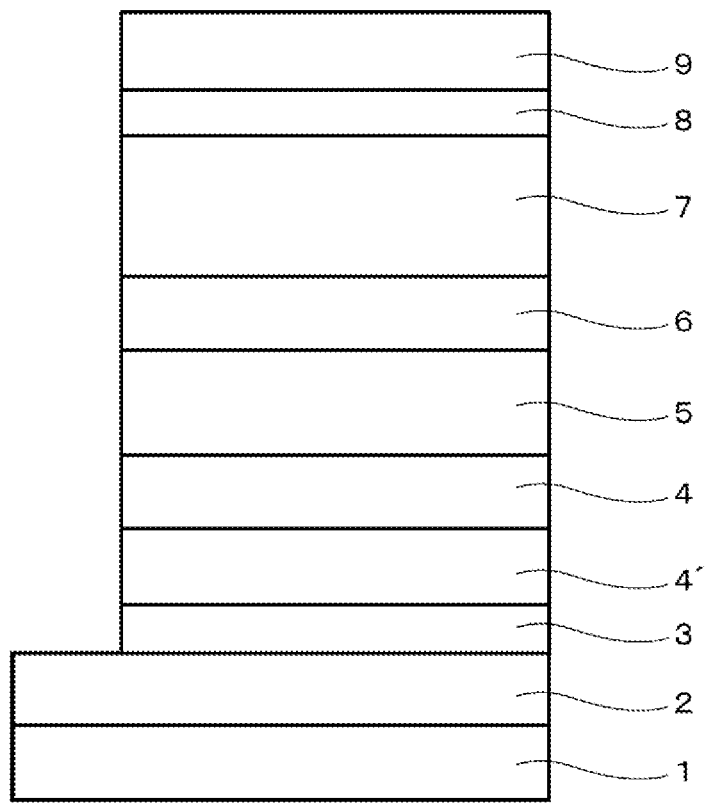
FIG. 1 represents the typical structure of the organic light-emitting-diode of the present invention.
Figure 2:
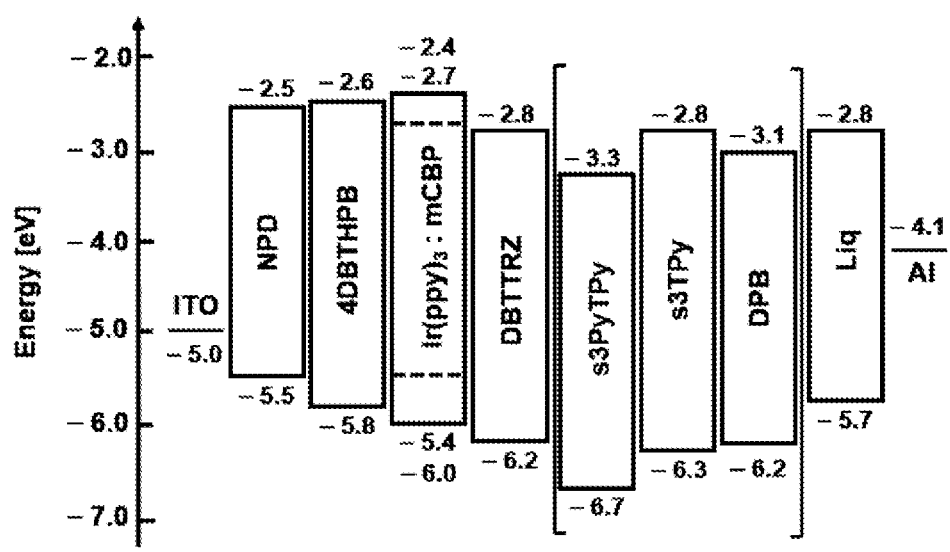
FIG. 2 represents an energy diagram of the hole transport material, the light-emitting material, the hole blocking material, and the electron injection material when s3PyTPy, s3TPy or DPB is used as the electron transport material composing the organic light-emitting-diode of the Examples.
Figure 3:
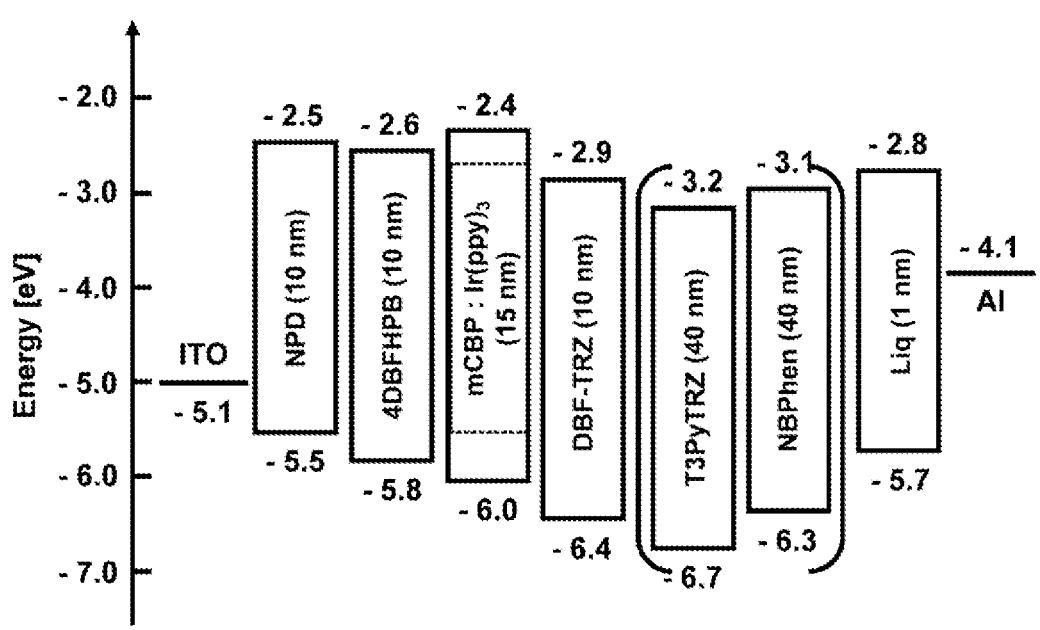
FIG. 3 represents an energy diagram of the hole transport material, the light-emitting material, the hole blocking material, and the electron injection material when T3PyTRZ or NBPhen is used as the electron transport material composing the organic light-emitting-diode of the Examples.

The compound having the nitrogen-containing six-membered aromatic ring structure (hereinafter referred to simply as "the nitrogen-containing six-membered ring compound") according to the present invention s substituted by at least three nitrogen-containing six-membered aromatic groups.

The nitrogen-containing six-membered ring compound of the present invention is represented by the following general formula (1).

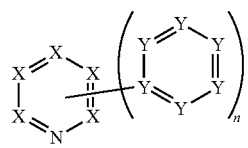

(1)

In the general formula (1), X and Y are carbon atoms substituted by R (—CR—) or nitrogen atoms. At least one of Ys is nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5. Six-membered rings formed by Ys may be the same or different each.

The nitrogen-containing six-membered ring compound of the present invention is represented by the following general formula (2).

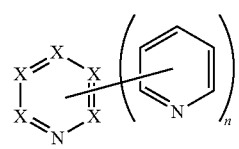

(2)

In the general formula (2), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5. The binding site for pyridyl group may be the same or different.

The nitrogen-containing six-membered ring compound of the present invention is represented by the following general formula (3).

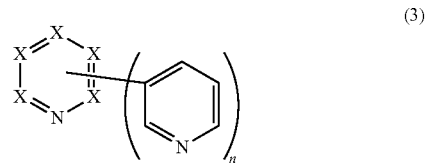

(3)

In the general formula (3), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5.

The nitrogen-containing six-membered ring compound of the present invention is represented by the following general formula (4).

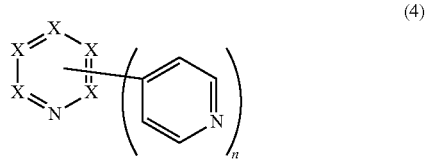

(4)

In the general formula (4), X is carbon atom substituted by R (—CR—) or nitrogen atom. R is hydrogen atom, deuterium atom, an alkyl group having 1 to 6 carbon atoms, an aryl group having 6 to 30 core carbon atoms, a heteroaryl group having 5 to 30 core atoms, a substituted or unsubstituted amino group, a substituted or unsubstituted silyl group, cyano group, or a halogen atom. When there are plural —CR— moieties, each R may be the same or different and adjacent Rs may be bonded to form a saturated or unsaturated ring. n is a natural number from 3 to 5.

The nitrogen-containing six-membered ring compound of the present invention represented by the following general formula (5) is the so-called quadruple pyridine derivative where a pyridine ring has pyridyl groups on its 2-, 4- and 6-positions.

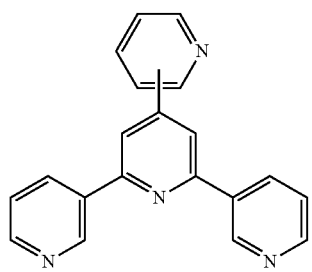

(5)

In the general formula (5), all or part of hydrogen atoms constituting the nitrogen-containing six-membered aromatic structure are substituted by an aryl group having 6 to 16 core carbon atoms.

The nitrogen-containing six-membered ring compound of the present: invention is also a quadruple pyridine derivative represented by the general formula (6).

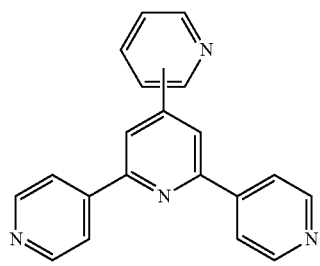

(6)

In the general formula (6), in one embodiment, all or part of hydrogen atoms constituting the nitrogen-containing six-membered aromatic ring structure are substituted by an aryl group having 10 to 18 core carbon atoms. In another embodiment, all or part of hydrogen atoms constituting only one of four pyridine rings are substituted by an aryl group having 6 to 18 core carbon atoms.

R is hydrogen atom, deuterium atom, an alkyl group having 1 to 6 carbon atoms, an aryl group having 6 to 30 core carbon atoms, a heteroaryl group having to 5 to 30 core atoms, a substituted or unsubstituted amino group, a substituted or unsubstituted silyl group, cyano group and a halogen atom.

The alkyl group having 1 to 6 carbon atoms includes methyl group, ethyl group, n-propyl group, isopropyl group, n-butyl group, isobutyl group, t-butyl group, n-pentyl group and n-hexyl group.

The aryl group having 6 to 30 core carbon atoms includes monocyclic and polycyclic aryl groups, such as phenyl group, 1-naphthyl group, 2-naphthyl group, 9-anthryl group, 9-phenanthryl group, 1-pyrenyl group, 5-naphthacenyl group, 1-indenyl group, 2-azulenyl group, 9-fluorenyl group, 9,9'-spirobifluorenyl group, 9,9'-diphenylfluorenyl group, terphenyl group, triphenylenyl group and quarterphenyl group. In the general formula (5), an aryl group having 6 to 16 core carbon atoms is preferable. In the general formula (6), an aryl group having 10 to 18 core carbon atoms is preferable, and an aryl group having 6 to 18 core carbon atoms is preferable when only one of four pyridine rings is substituted by the aryl group. The aryl groups may bond cyano group, fluorine atom and deuterium atom as far as they do not impair the advantageous effect of the present invention.

The aryl groups may bond a heteroaryl group having 5 to 30 core atoms described below. In other words, the heteroaryl group may be bonded to the quadruple pyridine moiety through aryl groups.

The heteroaryl group having 5 to 30 core atoms may be either a monocyclic or polycyclic heteroaryl group. Any of the followings can be used: thienyl group, pyrrolyl group, pyridyl group, pyrrolidyl group, piperidyl group, imidazolyl group, pyrazolyl group, pyrazyl group, pyrimidyl group, pyridazyl group, piperazyl group, triazinyl group, 2,4-diphenyltriazinyl group, oxazolyl group, isooxazolyl group, morpholyl group, thiazolyl group, isothiazolyl group, furanyl group, indolyl group, 9-phenylcarbazolyl group, carbazolyl group, quinolyl group, isoquinolyl group, benzimidazolyl group, quinazolyl group, phthalazyl group, purinyl group, pteridyl group, benzofuranyl group, dibenzofuranyl group, coumaryl group, benzothiophenyl group and dibenzothiophenyl group. Among these, 2-pyridyl group, 3-pyridyl group, 4-pyridyl group, terpyridyl group, pyrimidyl group, dibenzothiophenyl group, etc., are preferable. The heteroaryl groups can bond cyano group, fluorine atom, deuterium atom, etc., as far as they do not impair the advantageous effect of the present invention.

The substituted or unsubstituted amino group includes amino group, dimethylamino group and diethylamino group.

The substituted or unsubstituted silyl group includes trimethylsilyl group, triethylsilyl group, t-butyldimethylsilyl group, triisopropylsilyl group and t-butyldiphenylsilyl group.

The halogen atom includes fluorine, chlorine, bromine and iodine.

In the case where plural —CR— moieties exist, adjacent Rs may form a saturated or unsaturated ring, such as a saturated carbon ring and an unsaturated carbon ring. The saturated carbon ring includes cyclopropane, cyclobutane, cyclopentane, cyclohexane, cycloheptane, cyclooctane, cyclononane, cyclodecane, cycloundecane, cyclododecane. The unsaturated carbon ring includes cyclopropene, cyclobutene, cyclopentene, cyclohexene, cycloheptene and cyclooctene.

The nitrogen-containing six-membered ring compounds represented by the following general formulae (1) to (4) are, to be more concrete, preferably those having the following structural formulae.

TRZ2PyTPy

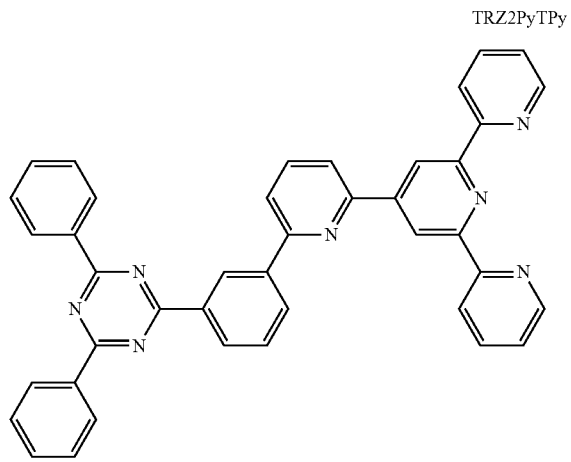

TRZ3PyTPy
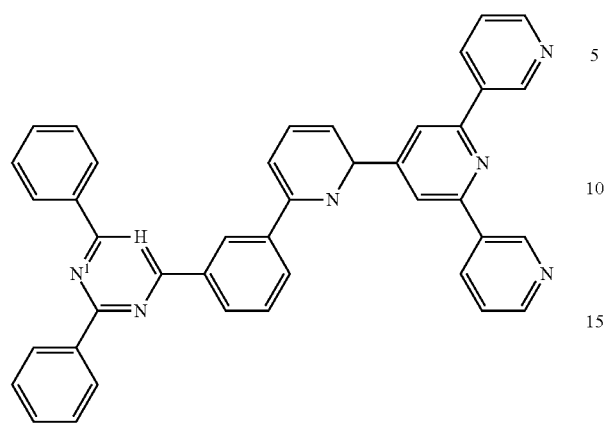
TRZ4PyTPy
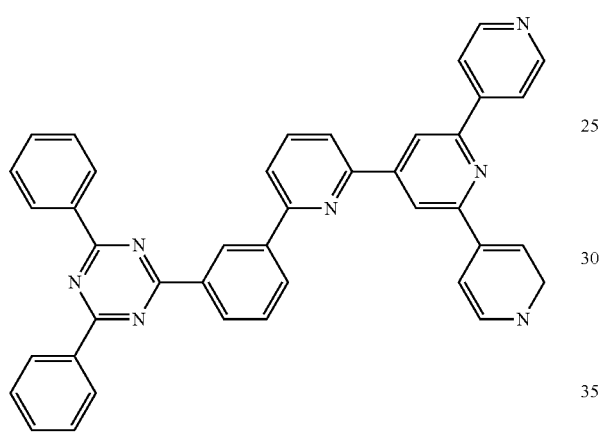
DPF2PyTPy
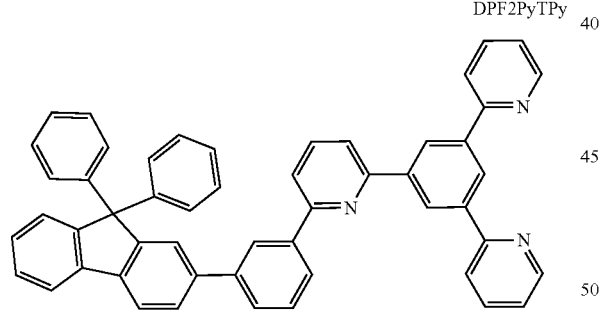
DPF3PyTPy
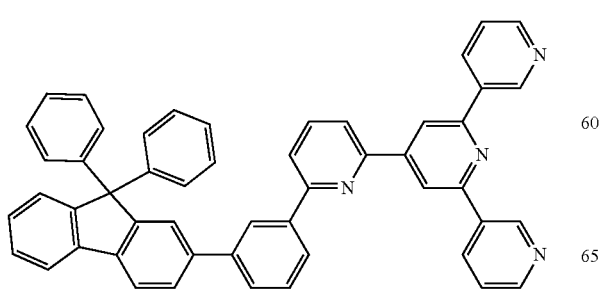
DPF4PyTPy
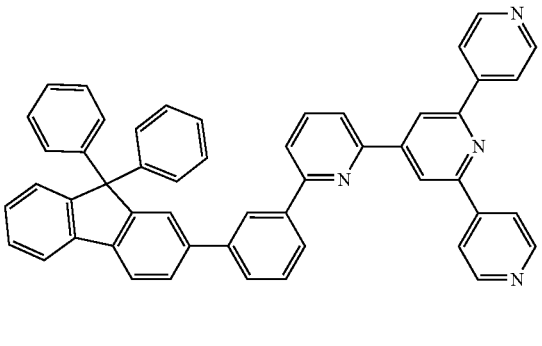
An2PyTPy
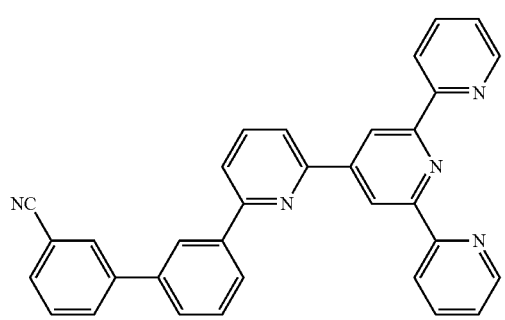
An3PyTPy
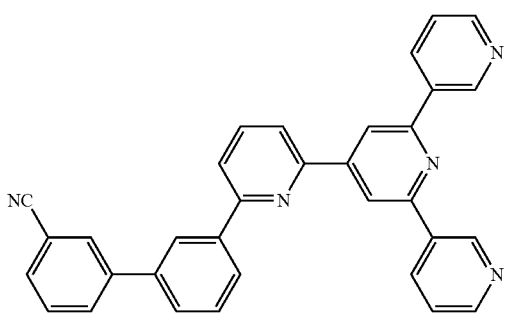
An4PyTPy
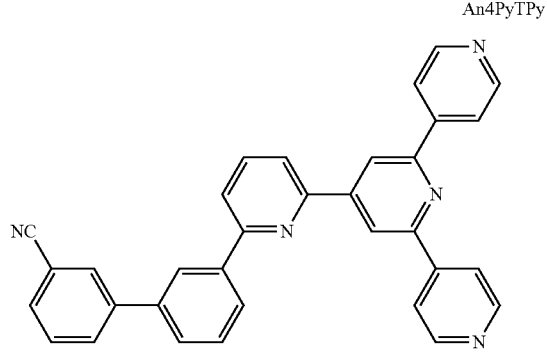

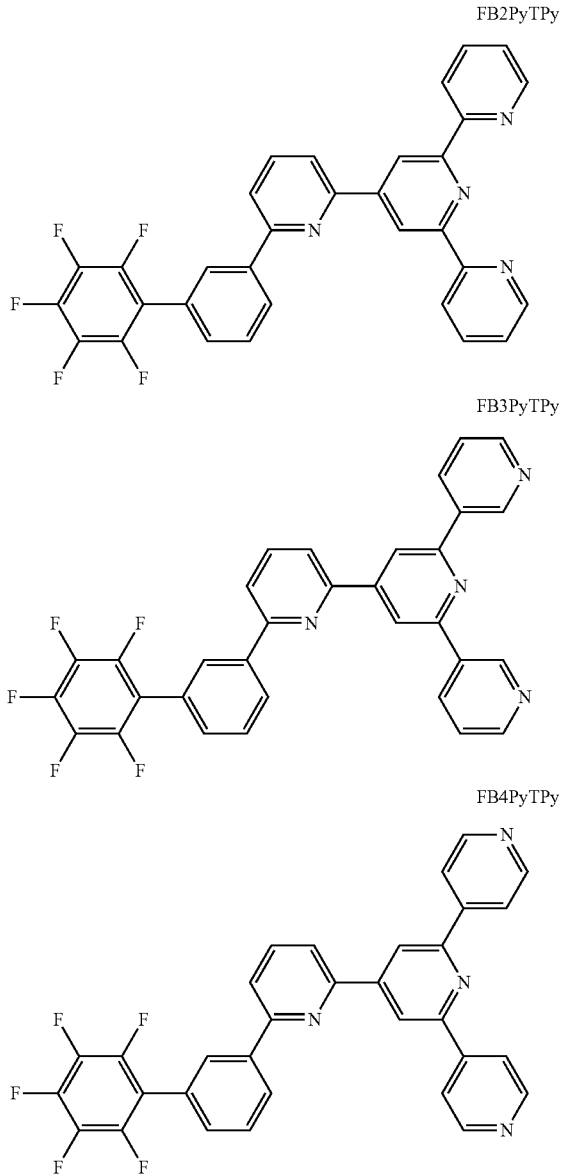
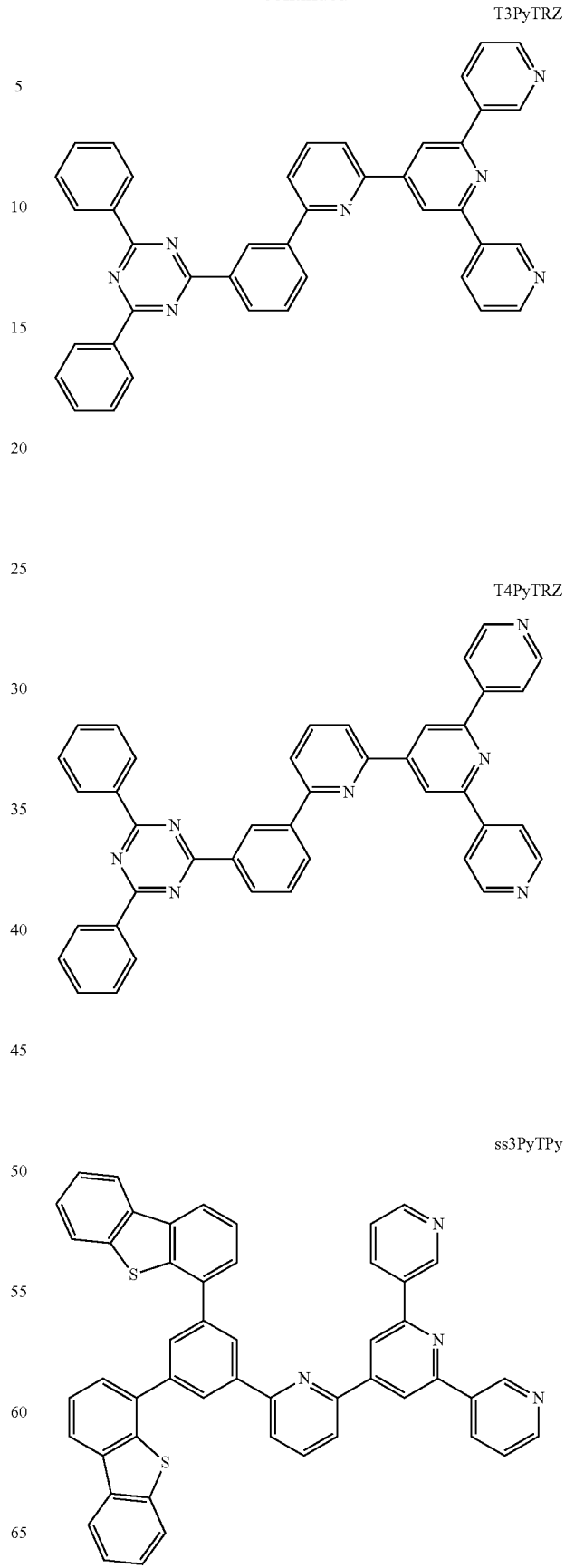

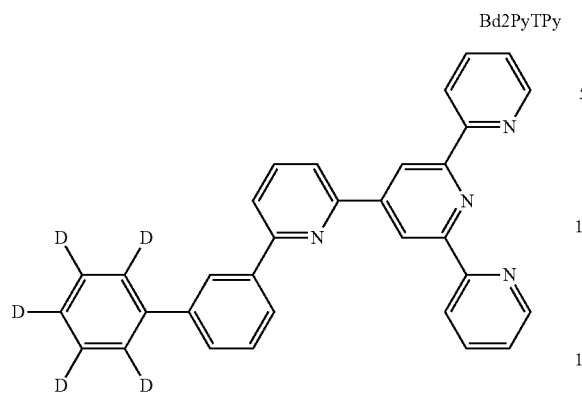
Bd2PyTPy
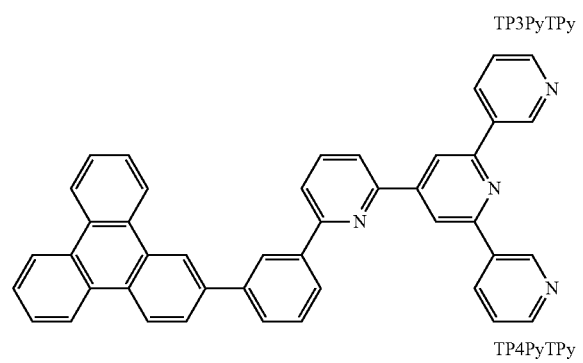
TP3PyTPy
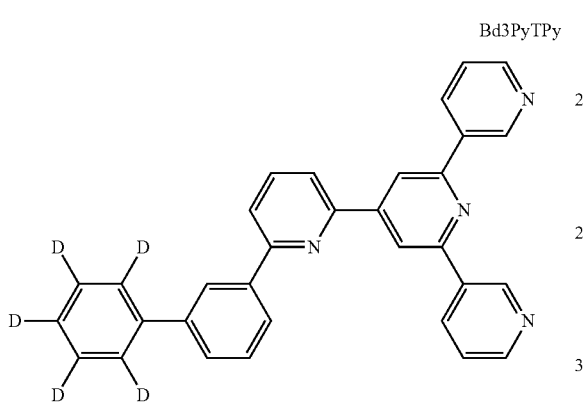
Bd3PyTPy
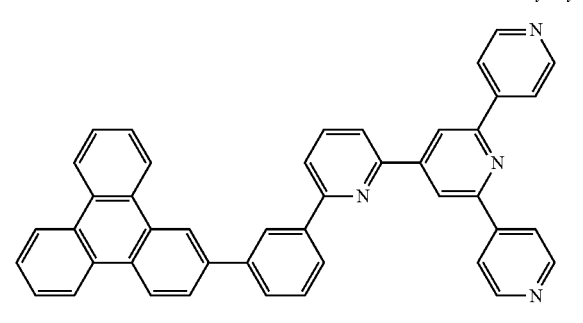
TP4PyTPy
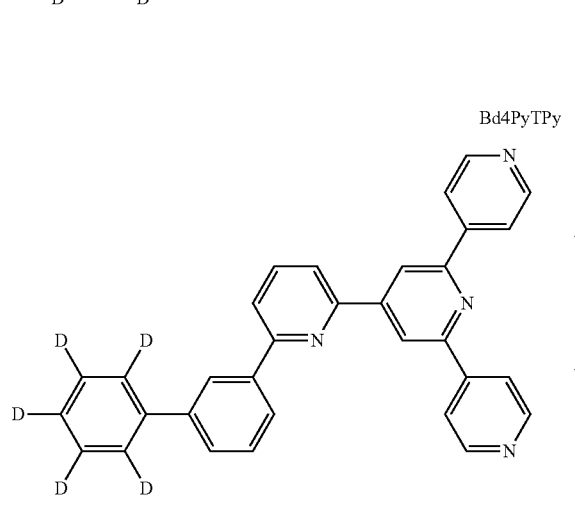
Bd4PyTPy
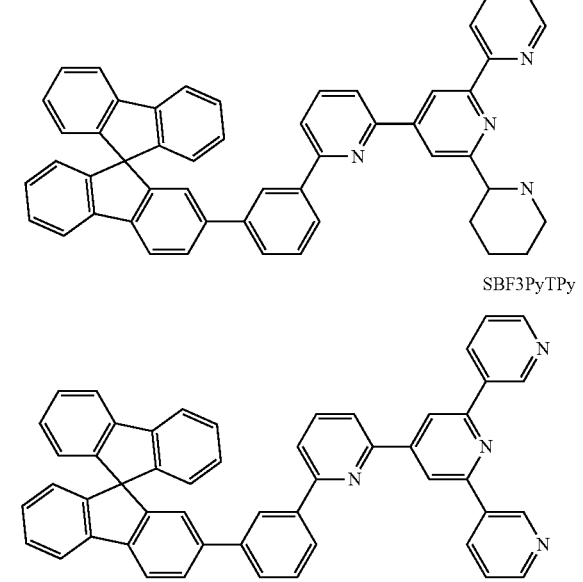
SBF2PyTPy
SBF3PyTPy
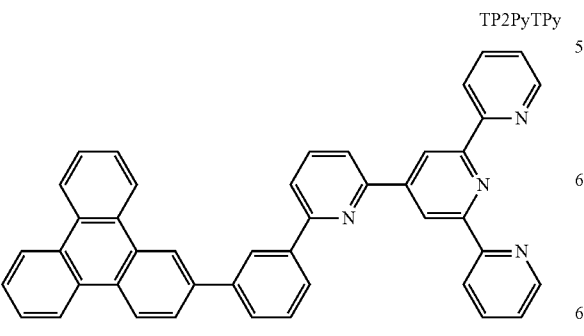
TP2PyTPy
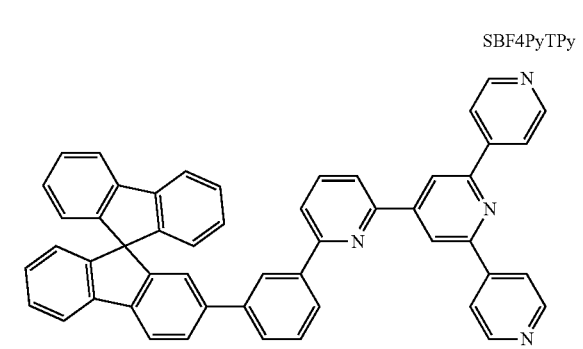
SBF4PyTPy 9PhCz2PyTPy
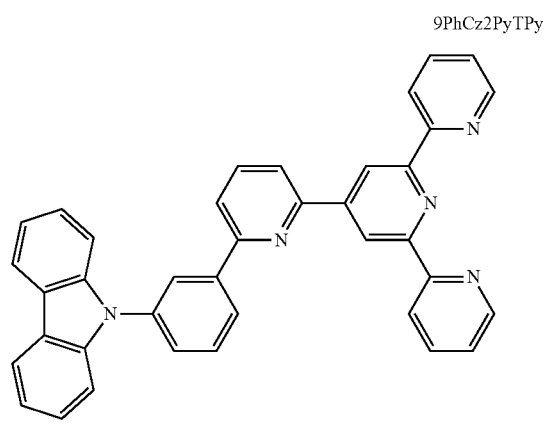
9PhCz3PyTPy
9PhCz4PyTPy
BDBF2PyTPy
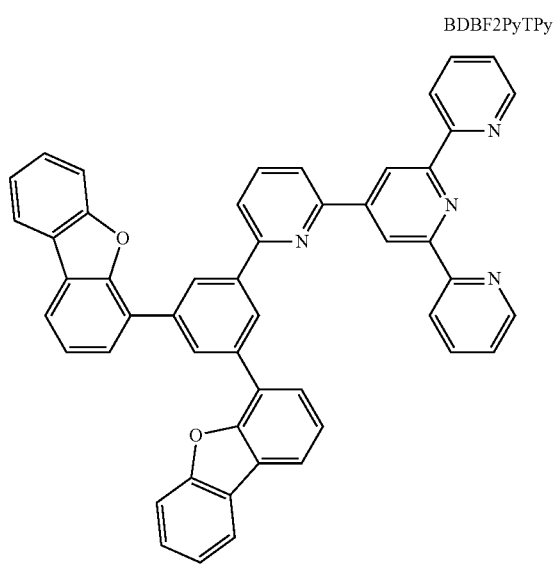
BDBF3PyTPy
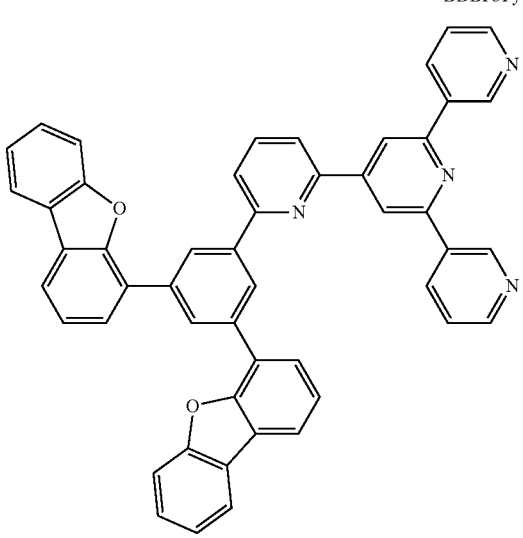
BDBF4PyTPy
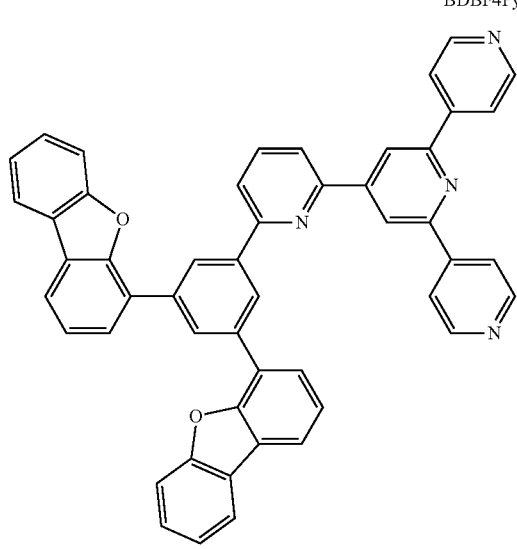

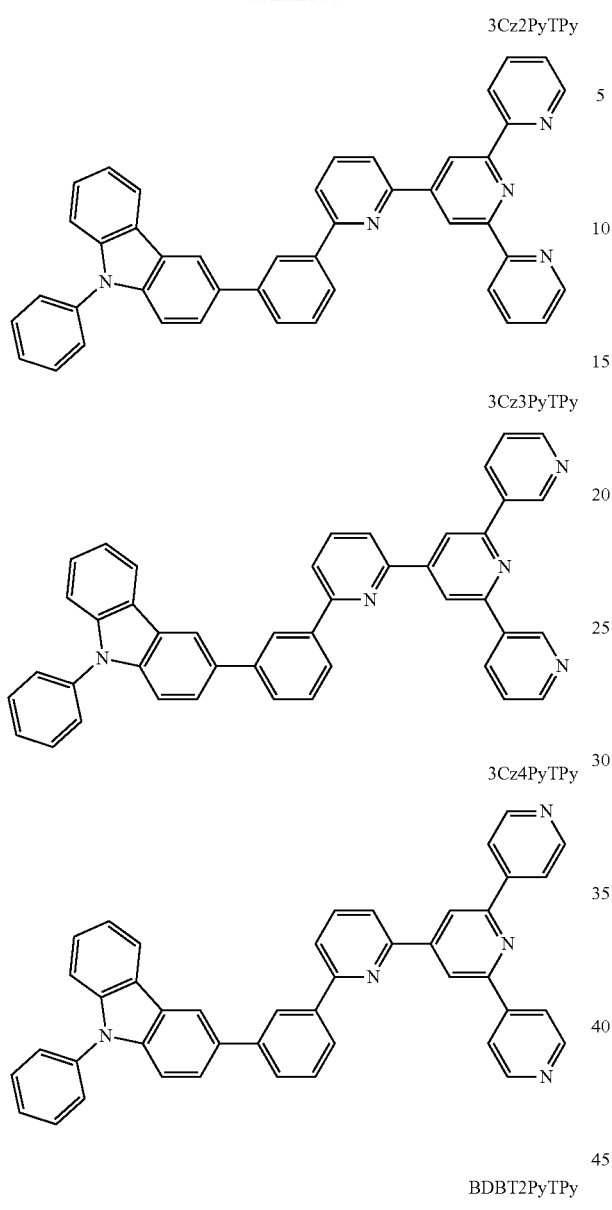
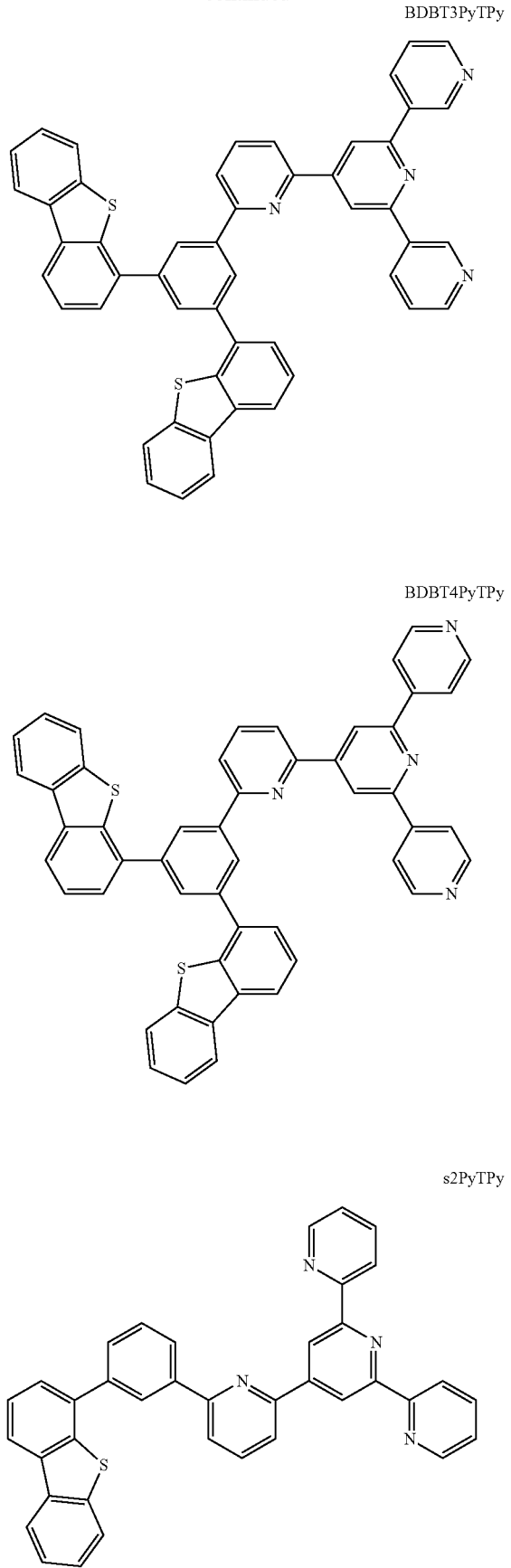

s3PyTPy
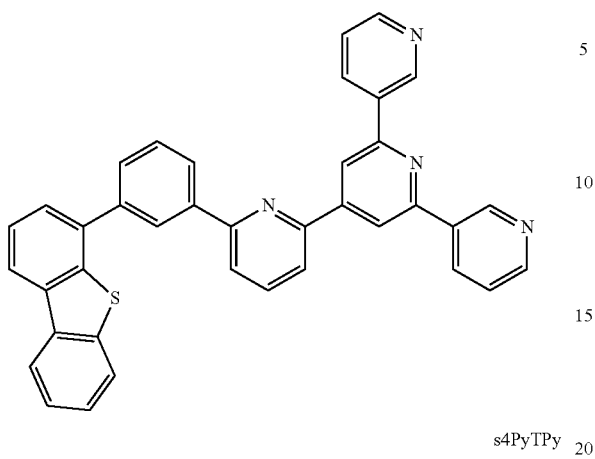
s4PyTPy
s3PyTPy
s4PyTPy
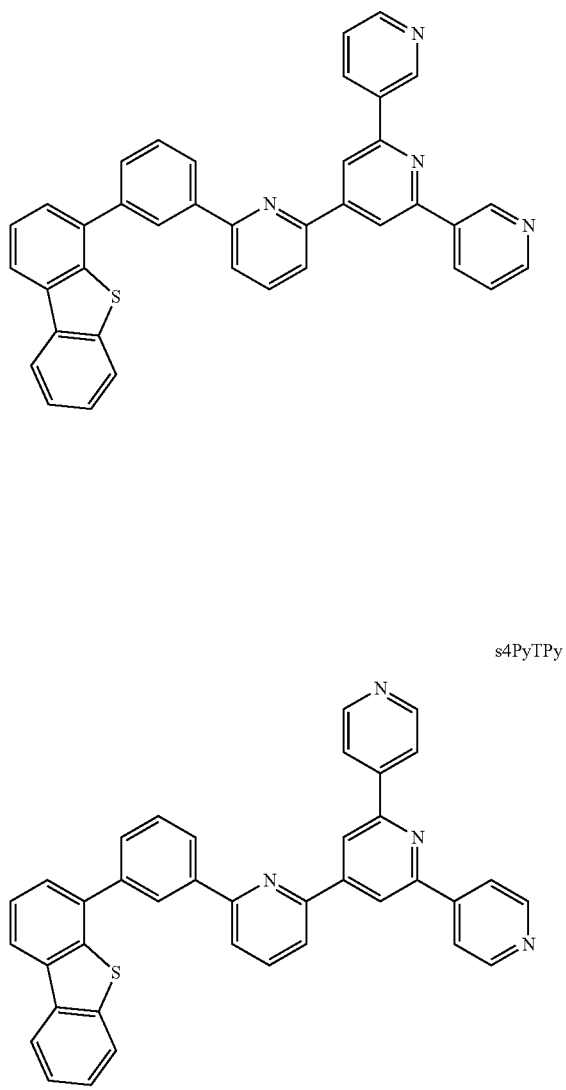
Among the compounds having the foregoing structural formulae, those having the structure represented by the general formula (5) or (6) are preferable, and more preferable examples of the quadruple pyridine derivative represented by the general formula (5) or (6) are s2PyTPy, s3PyTPy, s4PyTPy, T2PyTRZ, T3PyTRZ, T4PyTRZ, and ss3PyTPy.
s2PyTPy
T2PyTRZ
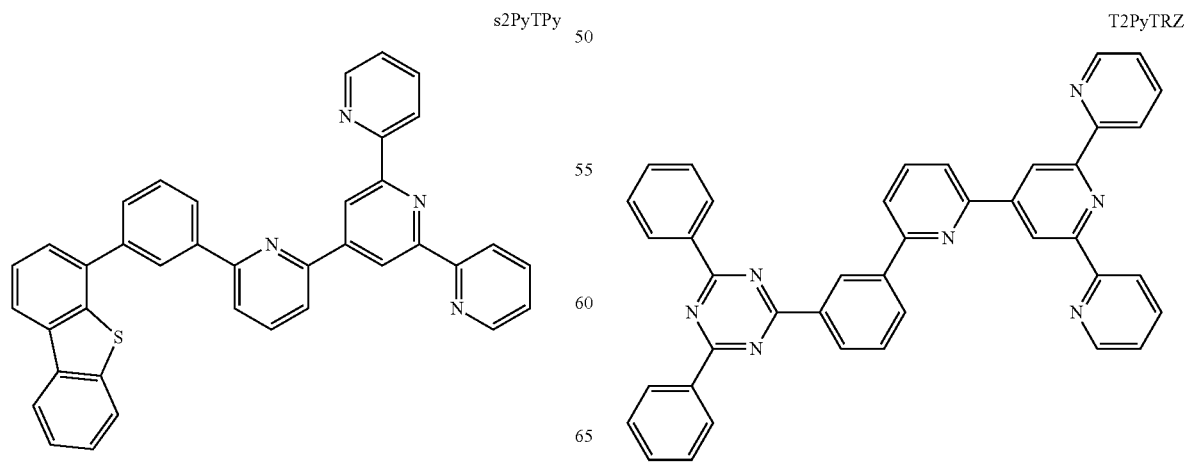

T3PyTRZ

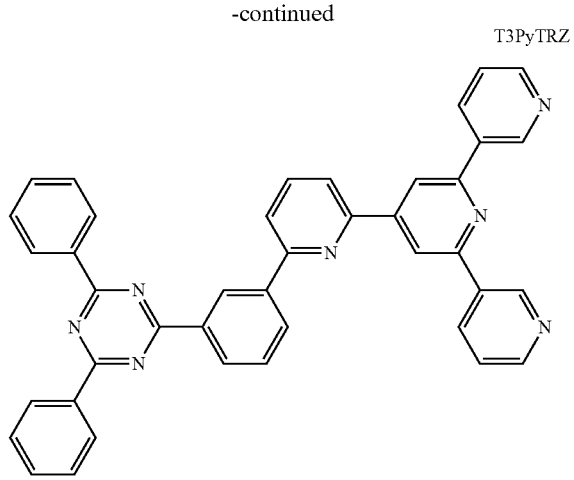

T4PyTRZ

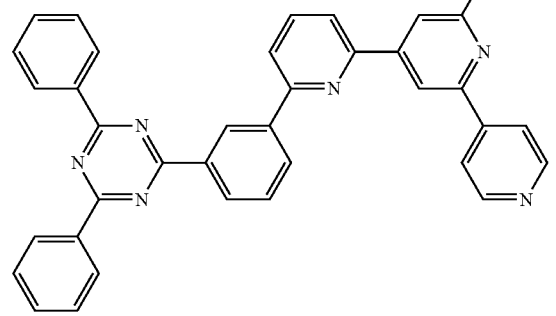

ss3PyTPy

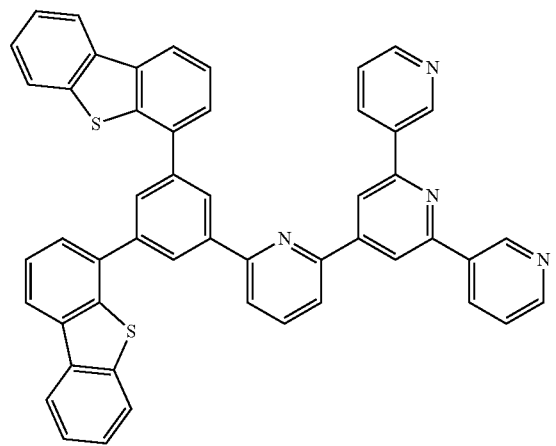

A variety of known methods can be used in synthesizing the nitrogen-containing six-membered ring compound of the present invention. As an example, s3PyTPy is synthesized as follows.

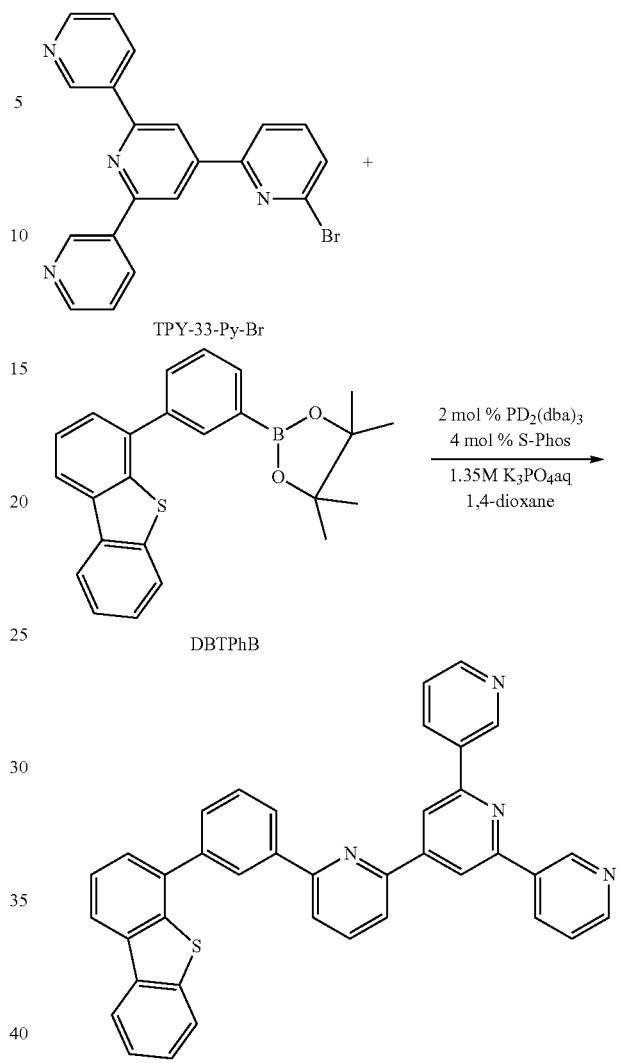

To a three-necked flask, TPY-33-Py-Br and DBTPhB are added in equimolar amounts, and thereto an aqueous solution of 1.35M tripotassium phosphate ($K_3PO_4$) and 1,4-dioxane are added. The mixture is bubbled with nitrogen, and 2 mol % $Pd_2$ (dba)$_3$ and 4 mol % S-Phos are added thereto. After the mixture being heated at reflux in a nitrogen atmosphere, the product is purified and the objective gray solid was obtained in a yield of 58%.

As for s2PyTPy, s3PyTPy and s4PyTPy, the LUMO is delocalized over the whole quadruple pyridine moiety in the presence of the electron-donating dibenzothiophene moiety, and forms an electronic state favorable to charge transfer to adjacent molecules. And their LUMO levels of −2.39 to −2.00 eV are deeper than a LUMO level of −1.68 eV of 2,2',2''-(1,3,5-phenylene)-tris(1-phenyl-1H-benzimidazole) (TPBi), which is a commerically available electron transport material. Therefore high electron injection characteristic can be expected. Because of the quasi-planar structure, the quadruple pyridine moiety shows intermolecular packing effect favorable to electron transport.

s3PyTPy has an ionization potential ($I_p$) of −6.7 eV; and a difference between the ionization potential ($I_p$) and the energy gap ($E_g$) is larger, namely the electron affinity (Ea) is deeper compared with those of known substances, such as 1,4-di(1,10-phenanthrolin-2-yl)benzene (DPB) and s3TPy. This suggests s3PyTPy has high electron injection characteristic.

The nitrogen-containing six-membered ring compound of the present invention has a x-conjugated system. The energy gap ($E_g$) can be controlled by adding an appropriate functional group to a x-conjugated molecule to change its electronic properties. In the present invention, the dibenzothiophene moiety and the quadruple pyridine moiety are introduced to the meta-position of the benzene ring to design the molecule so as to make the energy gap between the singlet excited state ($E_{S1}$) and the triplet excited state ($E_{T1}$) as small as possible, which enables the energy once transferred to the triplet excited state to revert to the singlet excited state again, and thereby fluorescent light can be extracted with high efficiency. The nitrogen-containing six-membered ring compound of the present invention can be suitably used for green phosphorescent device using Ir(ppy)$_3$ having a peak wavelength of 514 nm, for instance.

s3PyTPy has a melting point (Tm) of 247° C. and a decomposition temperature (Ta) of 471° C., which demonstrates that the nitrogen-containing six-membered ring compound has high thermal stability.

[Organic Light-Emitting-Diode]

The organic light-emitting-diode of the present invention has a pair of anode 2 and cathode 9, and at least one organic layer including a light-emitting layer between the pair of the electrodes. Any of the organic layers comprises the compound having the nitrogen-containing six-membered aromatic ring structure. The organic layers refers to the light-emitting layer 5, the hole blocking layer 6, the electron transport layer 7 and so on.

The organic light-emitting-diode of the present invention has a structure in which the nitrogen-containing six-membered ring compound is used as the electron transport layer. A typical structure of the organic light-emitting-diode is the anode 2 of ITO etc. formed on a substrate 1, the hole injection layer 3, the hole transport layer 4, 4', the light-emitting layer 5, the hole blocking layer 6, the electron transport layer 7, the electron injection layer 8 and a cathode 9 stacked in this order. An electron blocking layer may be further inserted between the hole transport layer 4 and the light-emitting layer 5. That is to say, several layers in the multilayer structures may be omitted, or for example, the electron injection layer 8 may be an electron injection/transfer layer which also functions as the electron transport layer 7. FIG. 1 shows the Examples of the present invention, and one embodiment of the organic light-emitting-diode is as follows: PTPD-1:PPBi having a thickness of 20 nm, as the hole injection layer 3; NPD having a thickness of 10 nm, as the hole transport layer 4; 4DBTHPB having a thickness of 10 nm, as the hole transport layer 4'; mCBP doped with 12 wt % Ir (ppy)$_3$, having a thickness of 15 nm, as the light-emitting layer 5; DBT-TRZ having a thickness of 10 nm, as the hole blocking layer 6; the nitrogen-containing six-membered ring compound of the present invention doped with 20 wt % Liq, having a thickness of 40 nm, as the electron injection/transport layer; Liq having a thickness of 1 nm, as the electron injection layer 8, and Al having a thickness of 100 nm, as the cathode 9 are formed on an ITO transparent electrode 2 on a glass substrate 1.

Transparent and smooth materials having a total light transmittance of at least 70% or more are used as the substrate 1. To be more concrete, the substrate 1 is flexible transparent substrate, such as glass substrate having a thickness of several microns or special transparent plastic.

The anode 2 has a role of injecting holes to the hole injection layer 3, the hole transport layer 4,4', and the light-emitting layer 5. In general, metal oxides, metals, alloys, and conductive materials having a work function of 4.5 eV or more are used as the anode 2 materials, while from the viewpoint of transmitting the emitted light, the materials having a total light transmittance of 80% or more are usually preferable. A specific example is transparent conductive ceramics such as indium tin oxide (ITO) and zinc oxide (ZnO), transparent conductive polymers such as conductive polymer, poly(3,4-ethylenedioxythiophene)/poly(4-styrene sulfonic acid) (PEDOT-PSS), polyaniline, and other transparent conductive materials. The anode 2 has a thickness of usually 5 to 500 nm and preferably 10 to 200 nm.

The anode 2 is formed by vapor deposition method, electron beam method, sputtering method, chemical reaction method, and coating method.

The cathode 9 has a function to inject electrons to the electron injection layer 8, the electron transport layer 7, and the light-emitting layer 5. In general, metals and alloys having a work function of 4.5 eV or less are appropriate for the cathode 9 materials. The metal used as the cathode 9 includes platinum, gold, silver, copper, iron, tin, zinc, aluminum, indium, chromium, lithium, sodium, potassium, calcium and magnesium, and among them, aluminum, lithium, sodium, potassium, calcium and magnesium are preferable. An example of the cathode made of an alloy is an electrode of an alloy of the foregoing low-work function metal and metals such as aluminum and silver, or a layer-structured electrode composed of the low-work function metal and metals such as aluminum and silver. Inorganic salts such as lithium fluoride can be also used as the layer-structured cathode. The cathode 9 has a thickness of usually 10 to 200 nm.

The cathode 9 is formed by vapor deposition method, electron beam method, sputtering method, chemical reaction method, and coating method.

The hole injection layer 3 is introduced to improve the luminous efficiency. To supply the current at low voltage, the hole injection layer 3 should be thin, or rather 1 to 20 nm-thick and uniform enough to avoid the generation of pinholes. The hole injection material includes PTPD-1: PPBi, triphenylamine-containing polymer: (4-isopropyl-4'-methyldiphenyliodonium tetrakis(pentafluorophenyl) borate (KLHIP:PPBI), triphenylamine-containing polyether ketone (TPAPEK), hexaazatriphenylenecarbonitrile (HATCN), poly(3,4-ethylenedioxythiophene) (PEDOT: PSS), phenylamine type, starburst amine type, poly(ether ketones) (PEK) and polyaniline. The foregoing compounds may form a layer of one kind alone, or a single layer may be formed with a mixture of two or more compounds. Or several compounds may form respective layers and make the layers into a multilayer.

The hole transport layer 4,4' which is placed between an anode 2 and a light-emitting layer 5, works for transporting holes from an anode 2 to a light-emitting layer 5 efficiently. The material having a small ionization potential, or specifically, the material which easily excites electrons from the HOMO and generates holes is used as the hole transport material. Specific examples include hexaphenylbenzene derivative (4DBTHPB), poly(9,9-dioctylfluorene-alt-N-(4-butylphenyl)diphenylamine) (TFB), 4,4'-cyclohexylidenebis[N,N-bis(4-methylphenyl)benzenamine] (TAPC), N,N'-diphenyl-N,N'-di(m-tolyl)benzidine (TPD), N,N'-di(1-naphthyl)-N,N'-diphenylbenzidine (NPD), 4,4',4"-tri-9-carbazolyltriphenylamine (TCTA) and 4,4',4"-tris [phenyl (m-tolyl)amino]triphenylamine. 4DBTHPB is preferable among these, because it has not only a sterically bulky structure and high triplet energy, but also has little interaction with luminescent materials. One of these compounds may form a layer of one kind, a mixture of two or more of the compounds may form a single layer, or several of the compounds may form respective layers of a multilayer.

Like other light-emitting layers for use in an organic light-emitting-diode, it is desirable that both a luminescent material and a host compound should be used for a light-emitting layer 5.

As for the luminescent material, the following phosphorescent materials are given: bis(2,3-diphenylquinoxazoline) iridium(dipivaloylmethane) ((DPQ)$_2$Ir(dpm)), tris(2-phenylpyridinato)iridium (III) (Ir(ppy)$_3$), bis[2-(4,6-difluorophenyl)pyridinato-C2,N] (picolinato)iridium (III) (FIrpic), tris[1-phenylisoquinoline-C2,N]iridium (III) (Ir(piq)$_3$) and bis(3-(trifluoromethyl)-5-(2-pyridyl)-pyrazolate) platinum (II) (Pt(fppz)$_2$).

Concerning the host compound, for example, 9,9'-diphenyl-9H,9'H-3,3'-dicarbazole (BCzPh), bis[2-(diphenylphosphino)phenyl]ether oxide (DPEPO), 3,6-bis(diphenylphosphoryl)-9-phenylcarbazole (P09), 4,4'-bis(N-carbazolyl)-1,1'-biphenyl (CBP), 3,3'-bis(N-carbazolyl)-1,1'-biphenyl (mCBP), tris(4-carbazoyl-9-ylphenyl)amine (TCTA), 2,8-bis(diphenylphosphoryl)dibenzothiophene (PPT), adamantane-anthracene (Ad-Ant), rubrene, 2,2'-bi(9,10-diphenylanthracene) (TPBA) and 1,4-di(1,10-phenanthrolin-2-yl)benzene (DPB) are given.

The hole blocking layer 6 has a role in enhancing the probability of recombining electrons with holes in the light-emitting layer 5 while transporting the electrons by preventing the holes from reaching the electron transport layer 7. The hole blocking material, for example, is 2-(3'-(dibenzo[b,d]thiophen-4-yl)-[1,1'-biphenyl]-3-yl)-4,6-diphenyl-1,3,5-triazine (DBT-TRZ), phenanthroline derivatives such as bathocuproine (BCP), metal complexes of quinolinol derivatives such as aluminum(III) bis(2-methyl-8-quinolinato)-4-phenylphenolate (BAlq), various rare earth complexes, oxazole derivatives, triazole derivatives, triazine derivatives, pyrimidine derivatives, oxadiazole derivatives, and benzoxazole derivatives. These materials can be also used as the materials for the electron transport layer 7. These compounds may form a layer of one kind alone, a mixture of two or more compounds may form a single layer, or several compounds may form respective layers of a multilayer.

The electron transport layer 7 which is placed between a cathode 9 and a light-emitting layer 5, has a role in transporting electrons from the cathode to the light-emitting layer efficiently. The nitrogen-containing six-membered ring compound of the present invention is used as the electron transport material. Other electron transport materials which have high electron affinity, in other words, the materials which make the energy level of the LUMO low and the excited electrons easy to exist are available. Examples include 3,3",5,5'-tetra(3-pyridyl)-1,1';3',1"-terphenyl (B3PyPB), 4,6-bis(3,5-di(pyridin-3-yl)phenyl)-2-methylpyrimidine (B3PyMPM), 2-(4-biphenylyl)-5-(p-t-butylphenyl)-1,3,4-oxadiazole (tBu-PBD), 1,3-bis[5-(4-t-butylphenyl)-2-[1,3,4]oxadiazolyl]benzene (OXD-7), 3-(biphenyl-4-yl)-5-(4-t-butylphenyl)-4-phenyl-4H-1,2,4-triazole (TAZ), bathocuproine (BCP), and 1,3,5-tris(1-phenyl-1H-benzimidazol-2-yl)benzene (TPBi). These compounds may form a layer alone, and two or more kinds mixed compounds may form a single layer or a multilayer.

The electron injection layer 8 in contact with the cathode has a role of transporting electrons. The electron injection material includes, for example, lithium fluoride (LiF), 8-hydroxyquinolinolato-lithium (Liq), and lithium 2-(2',2"-bipyridin-6'-yl)phenolate (Libpp). These compounds may form a layer of one kind alone, and two or more mixed compounds may form a single layer, and several compounds may form respective layers and make the layers into a multilayer.

The hole injection layer 3, the hole transport layer 4, the light-emitting layer 5, the electron transport layer 7 and the electron injection layer 8, which are formed on the substrate 1, are film-formed by vacuum deposition method or coating method. The vacuum deposition method includes resistance heating evaporation, electronic beam evaporation, sputtering method, and molecular stacking method. In a case where the vacuum deposition method is used, a vapor deposition substance is heated in an atmosphere of a reduced pressure of usually $10^{-3}$ Pa or less.

In a case where the coating method is used, materials for each layer are dissolved in, for example, chloroform, methylene chloride, dichloroethane, tetrahydrofuran, toluene, xylene, acetone, methyl ethyl ketone, ethyl acetate, butyl acetate, ethyl cellosolve acetate, water and so on, and then each layer is formed by a known coating method. The coating method includes bar coating method, capillary coating method, slit coating method, ink-jet coating method, spray coat method, nozzle coat method, and printing method. Each layer may be formed by the same coating method, or depending on the type of inks, optimal coating method may be applied severally.

The thickness of each organic layer between the anode 2 and the cathode 9 is usually 1 to 100 nm and preferably 1 to 50 nm, although some difference may depend on the resistance values and the charge mobility of constituent materials.

The organic light-emitting-diode of the present invention may be manufactured by for example the roll-to-roll process besides the single wafer process.

EXAMPLES

Hereinafter, the present invention will be described in detail with reference to Examples, but the present invention is not restricted to the Examples.

Synthesis of the Nitrogen-Containing Six-Membered Ring Compound

[Example 1] Synthesis of s3PyTPy

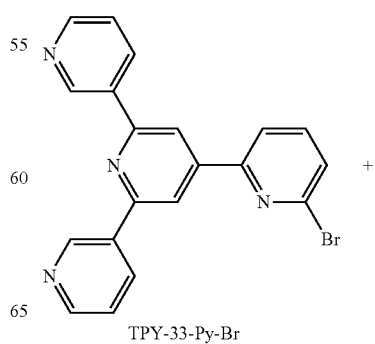

TPY-33-Py-Br

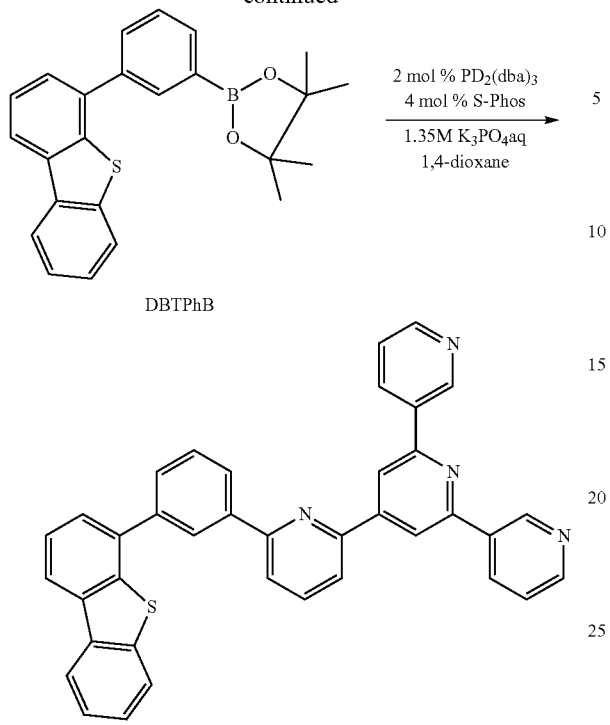

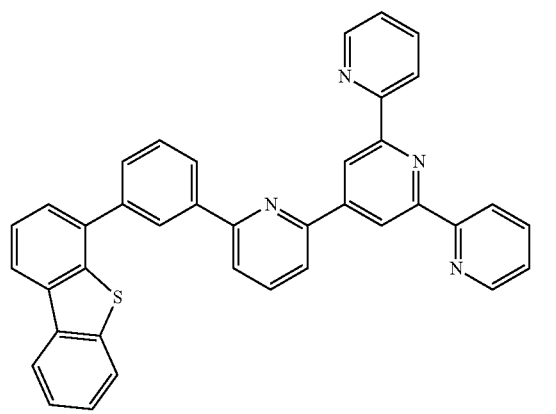

[Example 2] s2PyTPy

[Example 3] Synthesis of s4PyTPy

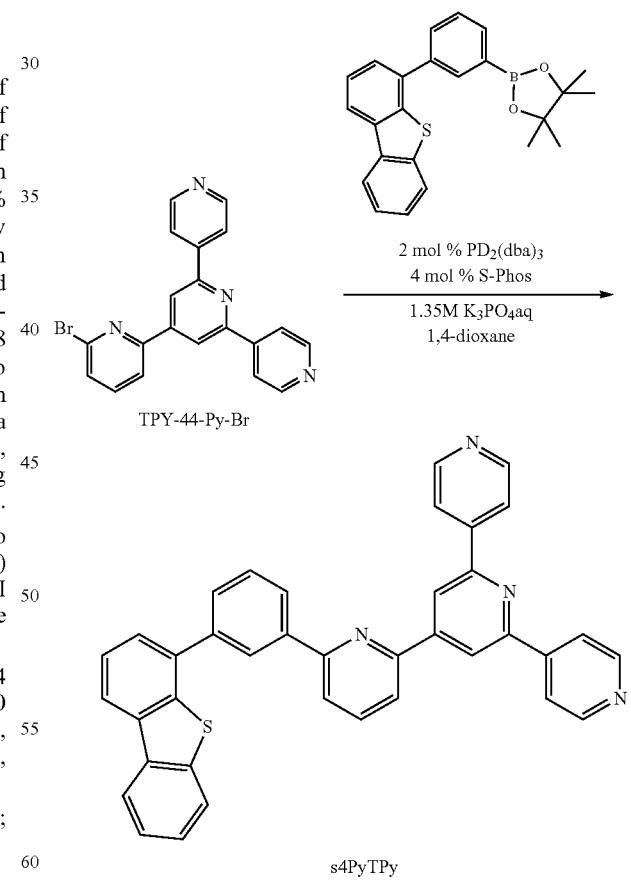

To a 200 mL three-necked flask, 2.74 g (7.05 mmol) of TPY-33-Py-Br, 3.27 g (8.46 mmol) of DBTPhB, 45 mL of water, 13.2 g of tripotassium phosphate and 130 mL of 1,4-dioxane were added, and the mixture was bubbled with nitrogen for 1 hour. The addition of 0.116 g of 4 mol % S-Phos and 0.129 g of 2 mol % $Pd_2(dba)_3$ was followed by heating to reflux at 104° C. for 21 hours in a nitrogen atmosphere. The precipitates were filtered out and subjected to ultrasonic cleaning in methanol. After filtration, remaining materials were dried under reduced pressure to give 3.28 g of a gray solid. Then, 220 mL of chloroform was added to ultrasonically dissolve the gray solid obtained. The solution was purified by silica gel column chromatography (silica gel: 500 cc, eluent: chloroform/methanol=100:0, 100:1, 100:3 and 100:10, v/v). After removal of the solvent, 2.3 g of s3PyTPy was obtained as white powder in a yield of 58%.

The s3PyTPy was further sublimed and was subjected to 1H-NMR measurement (Jeol JNM-EX270FT-NMR system) and elemental analysis (The PerkinElmer 2400 Series II CHNS/O Elemental Analyzer; CHN mode) The results are shown below.

$^1$H-NMR (400 MHz, CHLOROFORM-D) δ9.45 (d, J=1.4 Hz, 2H), 8.68-8.62 (m, 3H), 8.55-8.50 (m, 4H), 8.28-8.20 (m, 3H), 8.03-7.94 (m, 3H), 7.84 (d, J=7.8 Hz, 1H), 7.74 (dd, J=16.9, 7.8 Hz, 2H), 7.65-7.62 (m, 2H), 7.54-7.41 (m, 2H), 7.35-7.30 (m, 2H)

Anal. Calcd for $C_{38}H_{24}N_4S$: C, 80.26; H, 4.25; N, 9.85; S, 5.64%.

Found: C, 79.99; H, 4.17; N, 9.77; S, 5.56%.

The glass transition temperature ($T_g$) and the melting point ($T_m$) were determined by differential scanning calorimetry (DSC). The decomposition temperature ($T_d$) was determined by thermogravimetric analysis (TGA). $T_g$, $T_m$ and $T_d$ of s3PyTPy were 104° C., 247° C. and 471° C., respectively.

To a 50 mL three-necked flask, 0.78 g (2.00 mmol) of TPY-44-Py-Br, 0.93 g (2.4 mmol) of DBTBPhin, 13 mL of water, 3.74 g of tripotassium phosphate and 45 mL of 1,4-dioxane were added, and the mixture was bubbled with nitrogen for 1 hour. The addition of 0.033 g of 4 mol %

S-Phos and 0.037 g of 2 mol % Pd$_2$(dba)$_3$ was followed by heating to reflux at 104° C. for 36 hours in a nitrogen atmosphere. The precipitate after cooled down was filtered out and washed with water. The filtered substance was further dispersed and washed in methanol and dried under reduced pressure to give a yellowish white solid. After purified by silica gel column chromatography (eluent: CHCl$_3$/CH$_3$OH=100:0, 100:1, 100:3, and 100:5, v/v), white solid s4PyTPy (0.9 g, 79%) was obtained. The product obtained was recrystallized from toluene and methanol, giving a target compound with a purity of 99.5% or more. 1H-NMR (400 MHz, CHLOROFORM-D) δ 8.80-8.90 (1H), 8.61-8.70 (6H), 8.17-8.31 (3H), 8.07-8.14 (4H), 7.93-8.06 (3H), 7.80-7.87 (1H), 7.69-7.79 (2H), 7.59-7.68 (2H), 7.50-7.59 (1H), 7.39-7.50 (1H)

It is found that s4PyTPy has no glass transition temperature (Tg) but has a melting point ($T_m$) of 287° C. and a decomposition temperature ($T_d$) of 479° C.

[Example 4] Synthesis of ss3PyTPy (i) Step 1

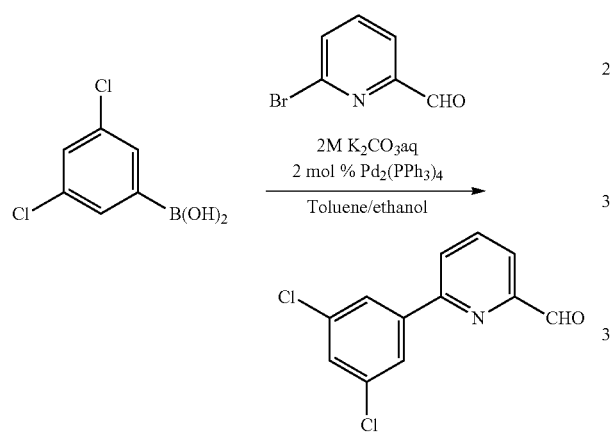

To a 200 mL three-necked flask equipped with a Dimroth condenser, 1.91 g (10 mmol) of 3,5-dichlorophenylboronic acid, 1.86 g (10 mmol) of 6-bromo-2-pyridinecarboxyaldehyde, 40 mL of toluene, 20 mL of ethanol, and 20 mL of an aqueous solution of 2M potassium carboxylate were added in order. The mixture was strongly stirred and heated at reflux for 19 hours. The ethanol was concentrated and the residual solution was extracted from toluene and a saturated saline solution. The extract was dried with magnesium sulfate and concentrated. The product was purified by silica gel column chromatography (eluent: toluene) to give 0.9 g of a white solid in a yield of 36%.

(ii) Step 2

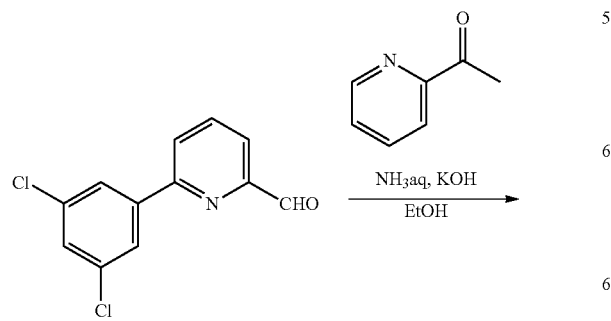

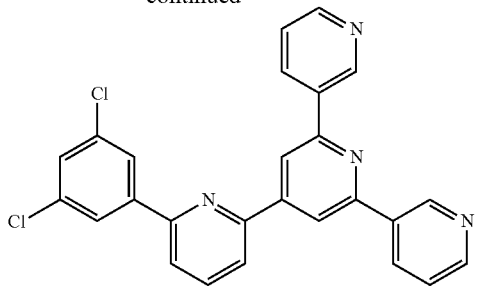

To a 200 mL Erlenmeyer flask, 0.75 g (3 mmol) of the compound synthesized in step 1, 30 mL of ethanol (special grade), 1.0 mL (9 mmol) of 3-acetylpyridine, 0.5 g of potassium hydroxide, and 30 mL of 28% ammonia water were added in order. The mixture was strongly stirred at normal temperature (24° C. and 42% humidity) for 17 hours under atmospheric pressure. The reaction solution was filtered out while being washed with water and ethanol. The filtered substance was ultrasonically washed in methanol and filtered out to give a white solid. After dried under reduced pressure, the white solid was purified by silica gel column chromatography (eluent; a mixed solvent of chloroform:methanol=100:1, 100:3, and 100:5, v/v) to give a white solid. Then, the white solid was recrystallized from toluene and ethanol, which finally provided 1.72 g of the target compound in a yield of 26.9%. The purity was 99.5% or more.

(ii) Step 3

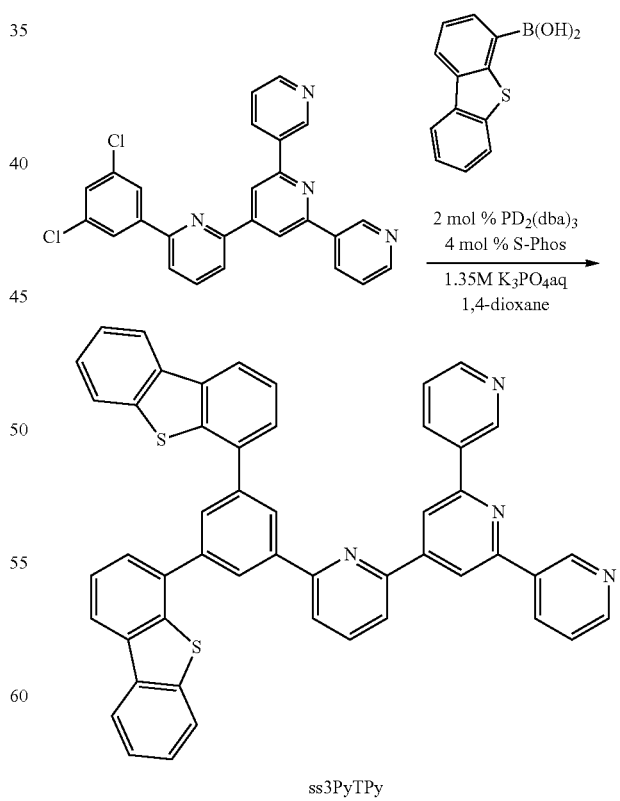

ss3PyTPy

To a 100 mL three-necked flask equipped with a Dimroth condenser, 0.91 g (2.0 mmol) of the compound synthesized in step 2, 1.82 g (4 mmol) of dibenzothiophene-4-boronic acid, 45 mL of 1,4-dioxane, and 10 mL of an aqueous solution of 1.35M tripotassium phosphate were added in order, and the mixture was strongly stirred and heated at reflux for 19 hours. The precipitate after cooled down was filtered out under reduced pressure. The filtered substance was ultrasonically washed in methanol, and filtered out. The white solid obtained was dried under reduced pressure. Next, 1.5 g of a white solid thus obtained was purified by silica gel column chromatography (eluent: a mixed solvent of chloroform/methanol=100:1, 100:3, and 100:5, v/v) to provide a white solid, which was recrystallized from a mixed solvent of toluene and ethanol several times. Further recrystallization from a mixed solvent of chloroform and methanol (100:1, v/v) gave 0.51 g of a white solid in a yield of 34%.

ss3PyTPy had a molecular weight of 750, a glass transition temperature (Tg) of 150° C., a melting point ($T_m$) of 308° C., and a decomposition temperature ($T_d$) of 545° C.

The evaluation results of optical properties of s3PyTPy, s4PyTPy and ss3PyTPy are shown in Table 1.

TABLE 1

| Compounds | $I_p{}^{a)}$ [eV] | $E_g{}^{b)}$ [eV] | $E_a{}^{c)}$ [eV] |
|---|---|---|---|
| s3PyTPy | −6.4 | 3.4 | −3.0 |
| s4PyTPy | −6.5 | 3.4 | −3.1 |
| ss3PyTPy | −6.3 | 3.4 | −2.9 |

$^{a)}$Obtained from a photoelectron yield spectroscopy (PYS).
$^{b)}$Taken as the point of intersection of the normalized absorption spectra.
$^{c)}$$E_a$ was calculated using $I_p$ and $E_g$.

[Comparative Example 1] s3TPy

The compound represented by the following structural formula was used.

s3TPy

[Comparative Example 2] DPB

The compound represented by the following structural formula was used.

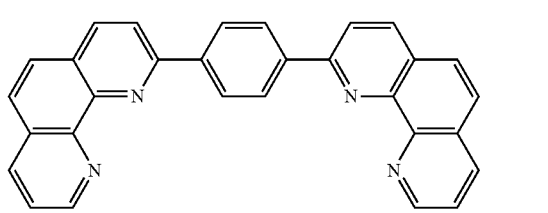

DPB

[Comparative Example 3] Ph-QYY-4Py

The quadruple pyridine derivative represented by the following structural formula was used.

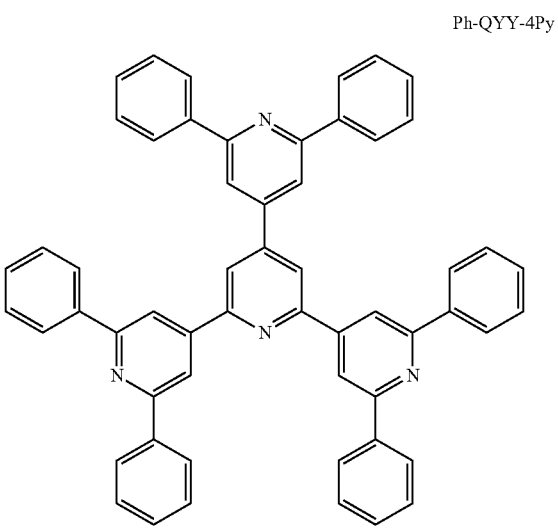 [SMILES: c1ccc(-c2cc(-c3cc(-c4cc(-c5ccccc5)nc(-c5ccccc5)c4)nc(-c4cc(-c5ccccc5)nc(-c5ccccc5)c4)c3)cc(-c3ccccc3)n2)cc1]

Ph-QYY-4Py

[Comparative Example 4] TrP-QYY-3Py-1

The quadruple pyridine derivative represented by the following structural formula was used.

TrP-QYY-3Py-1

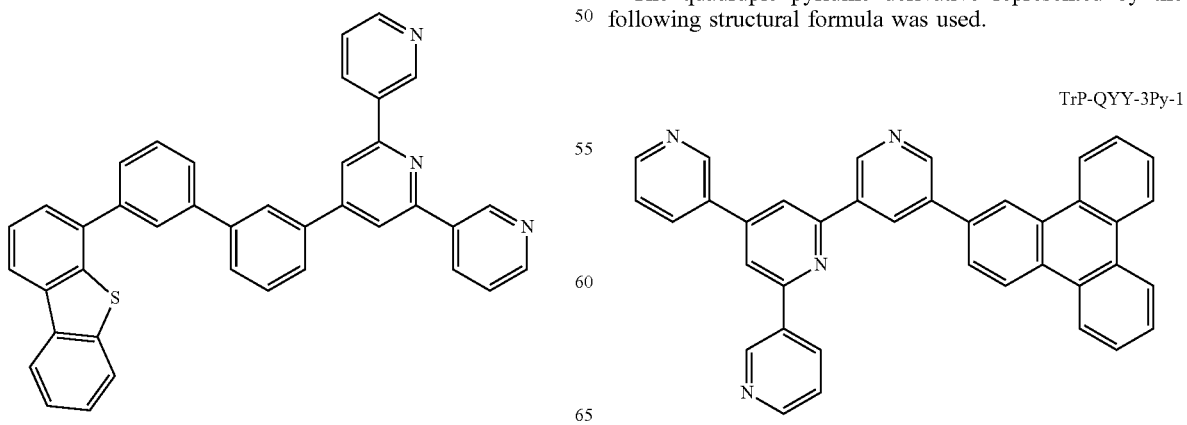

[Comparative Example 5] TrP-QYY-3Py-2

The quadruple pyridine derivative represented by the following structural formula was used.

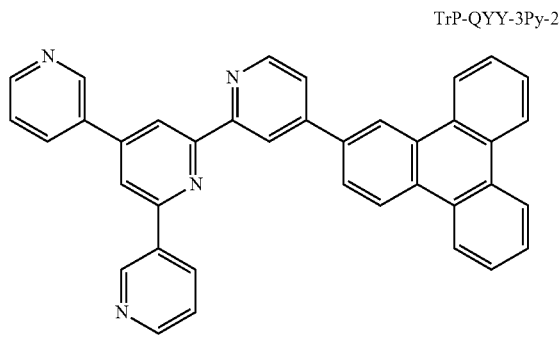 [SMILES: c1cncc(-c2cc(-c3cccnc3)nc(-c3cc(-c4ccc5c6ccccc6c6ccccc6c5c4)ccn3)c2)c1]

TrP-QYY-3Py-2

[Quantum Chemical Calculation]

The quantum chemical calculation using density functional theory (DFT) (RB3LYP/6-311+G(d,p)//B3LYP/6-31G (d) level) and time-dependent density-functional theory (TD-DFT) (RB3LYP/6-31G (d)//RB3LYP/6-31G (d) level) was carried out to investigate s3PyTpy, s2PyTPy and s4PyTPy of Examples 1 to 3.

The results of quantum chemical calculations of s2PyTpy, s3PyTPy and s4PyTPy are shown in Table 2.

TABLE 2

| Compound | Molecular Weight (Mw) | $E_T{}^{a)}$ (eV) | HOMO/LUMO/$E_g{}^{b)}$ (eV) |
|---|---|---|---|
| s2PyTPy | 568.69 | 2.83 | −6.02/−2.00/4.02 |
| s3PyTPy | 568.69 | 2.85 | −5.93/−2.31/3.62 |
| s4PyTPy | 568.69 | 2.90 | −6.20/−2.39/3.81 |

$^{a)}$The lowest triplet energy ($E_T$) obtained from the TD-DFT calculation (RB3LYP/6 − 31G(d)//RB3LYP/6 − 31G(d) level).
$^{b)}$HOMO, LUMO and HOMO-LUMO energy gap ($E_g$) obtained from the DFT calculations (RB3LYP/6 − 311 + G(d, p)//B3LYP/6 − 31G(d) level).

[Evaluation of Optical Properties]

The optical properties in the solid state were evaluated in light of the application to an organic semiconductor device.

A thin film of s3PyTPy was formed by vacuum deposition method. The ionization potential ($I_p$) of the thin film was measured by photoelectron yield spectroscopy (PYS) (ionization potential measuring device manufactured by Sumitomo Heavy Industries, Ltd.).

The ultraviolet visible (UV-vis) absorption spectrum was measured using UV-3150 manufactured by Shimadzu Corporation, and the energy gap ($E_g$) was calculated from a rising wavelength in the normalized spectrum.

The electron affinity ($E_a$) was roughly estimated by a difference between the ionization potential ($I_p$) and the energy gap ($E_g$).

As for s3PyTPy, $I_p$ was −6.7 eV, $E_g$ was 3.4 eV and $E_a$ was −3.3 eV.

[Organic Light-Emitting-Diode Using the Nitrogen-Containing Six-Membered Ring Compound]
<Manufacture of an Elemental Device>

An organic light-emitting-diode was manufactured using a material prepared by doping s3PyTPy synthesized in Example 1 with 50 mol % 8-hydroxyquinolatolithium (Liq), as an electron transport material.

An organic light-emitting-diode was manufactured using an electron transport material prepared by doping the compounds of Comparative Examples 1 to 5 with 50 mol % Liq. Among the layers constituting the organic light-emitting-diode, the polymer buffer layer, or PDPD-1:PPBI layer was formed by coating, and the other layers were formed by vapor deposition.

The structure of the elemental device is shown below (FIG. 1). ETM represents an electron transport material. [ITO/PTPD-1: tetrakis(pentafluorophenyl)borate (PPBI) (20 nm)/N,N'-di(1-naphthyl)-N,N'-diphenyl-(1,1'-biphenyl)-4,4'-diamine (NPD) (10 nm)/4DBTZHPB (10 nm)/mCBP:12 wt % Ir(ppy)$_3$ (15 nm)/DBT-TRZ (10 nm)/ETM:20 wt % Liq (40 nm)/Liq (1 nm)/Al (100 nm)]

ETM: s3PyTPy, s3TPy, DPB, Ph-QYY-4Py, TrP-QYY-3Py-1 or TrP-QYY-3Py-2

Materials used for the elemental device are shown below.

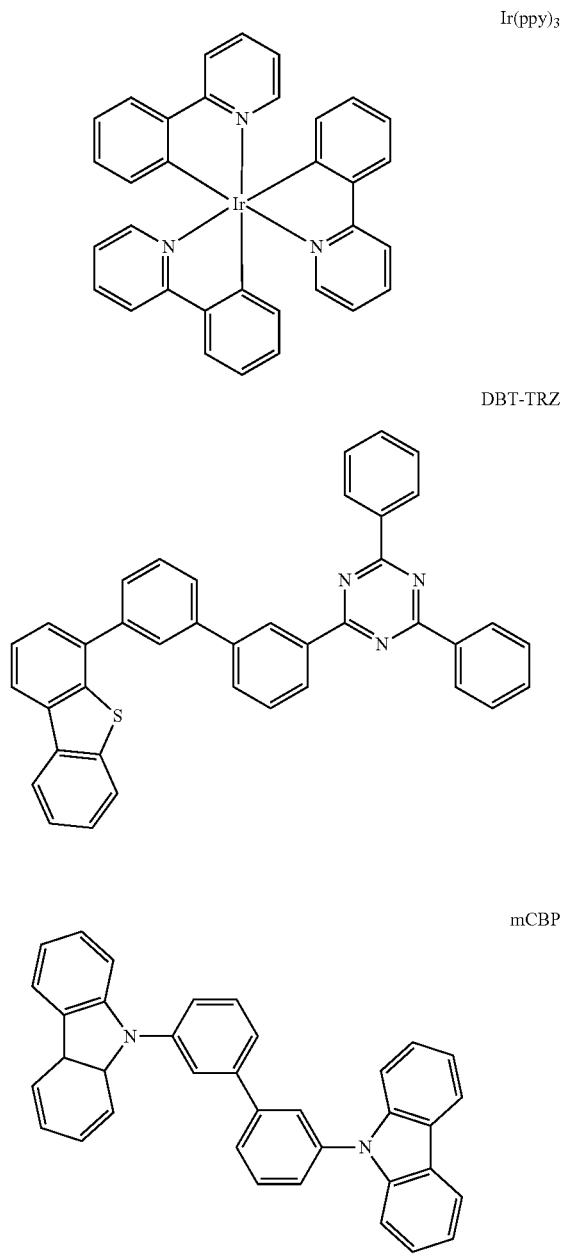

4DBTHPB

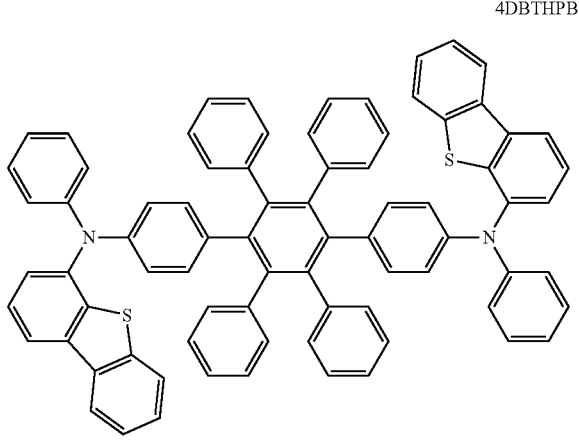

NPD

Liq

<Evaluation of an Elemental Device>

The EL spectra of s3PyTPy of Example 1, s3TPy of Comparative Example 1, DPB of Comparative Example 2, Ph-QYY-4Ph of Comparative Example 3, TrP-QYY-3Py-1 of Comparative Example 4, and TrP-QYY-3Py-2 of Comparative Example 5 were measured using the PHOTONIC MULTI-CHANNEL ANALYZER PMA-1 manufactured by Hamamatsu Photonics K.K. The evaluation results of the elemental device are shown in Table 3.

TABLE 3

| ETM | | V1000/$\eta_{p,1000}$/$\eta_{c,1000}$/$\eta_{ext,1000}$[c] [V/lm W$^{-1}$/cd A$^{-1}$/%] | LT$_{70}$[d] [h] |
|---|---|---|---|
| Ex. 1 | s3PyTPy | 4.11/61.3/80.2/22.1 | 144 |
| Comp. Ex. 1 | s3TPy | 4.13/61.3/80.5/22.5 | 86 |
| Comp. Ex. 2 | DPB | 3.72/62.3/73.7/20.6 | 70 |
| Comp. Ex. 3 | Ph-QYY-4Py | 4.22/58.3/78.3/22.1 | 46 |
| Comp. Ex. 4 | TrP-QYY-3Py-1 | 4.13/61.4/80.8/22.6 | 83 |
| Comp. Ex. 5 | TrP-QYY-3Py-2 | 4.14/60.9/80.3/22.2 | 82 |

[c] Voltage (V), power efficiency ($\eta_p$), current efficiency ($\eta_c$) and external quantum efficiency ($\eta_{ext}$) at 1000 cdm$^{-2}$.
[d] Operational lifetime until luminance reduces to 70% of an initial luminance of 1000 cdm$^{-1}$ at 25 mAcm$^{-2}$.

[Synthesis of the Nitrogen-Containing Six-Membered Ring Compound]

[Example 5] Synthesis of T3PyTRZ (i) Synthesis of TPY33PyBr

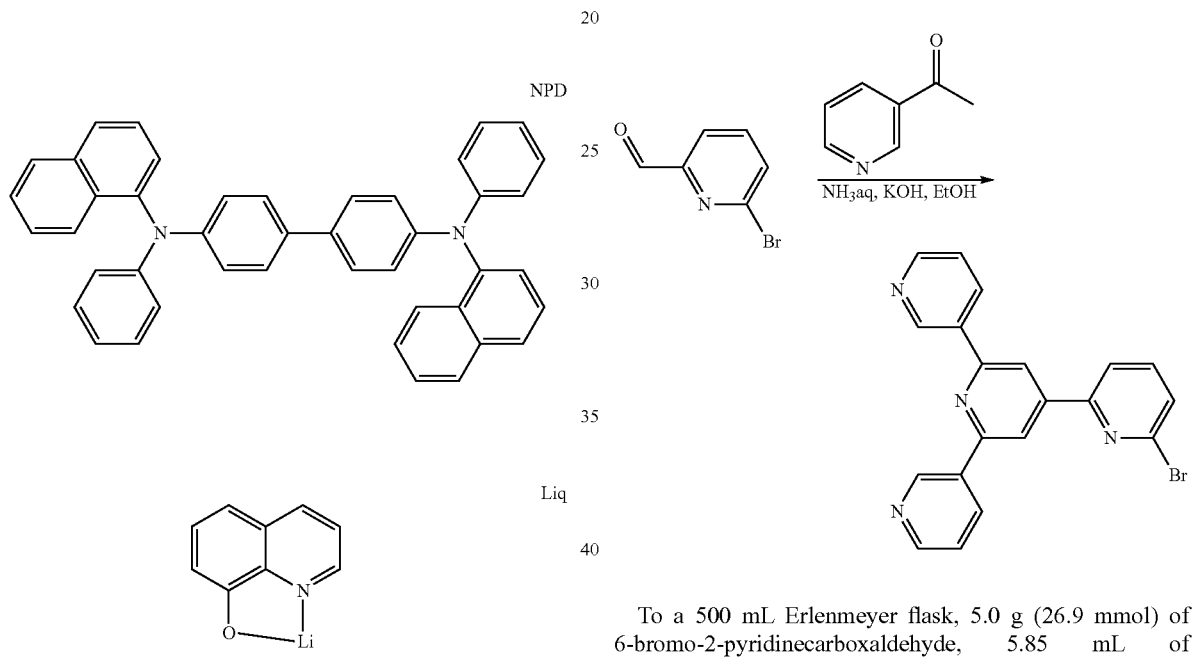

To a 500 mL Erlenmeyer flask, 5.0 g (26.9 mmol) of 6-bromo-2-pyridinecarboxaldehyde, 5.85 mL of 3-acetylpyridine, 136 mL of ammonia water, 201 mL of ethanol, and 1.5 g of potassium hydroxide were added in order, and the mixture was stirred. At first, the mixture was a transparent yellow solution, but turned transparent red immediately after being stirred, and then the solution turned turbid yellow. After the solution was stirred for 25 hours, the thin-layer chromatography (TLC) confirmed the disappearance of starting materials and a spot of Rf-value 0.25 corresponding to the target compound, and the reaction was stopped. The precipitate was filtered out and washed with ethanol. The pale yellow solid thus obtained was dispersed and washed in 100 mL of methanol to provide 2.21 g of white solid TPY33PyBr in a yield of 21%.

Next, the product was recrystallized from toluene. To a 300 mL round-bottom flask, 0.45 g of TPY33PyBr and 10 mL of toluene were added, and the mixture was stirred at approximately 100 to 110° C. using an oil bath. Toluene was added by 5 mL to the flask until 25 mL. The solution became saturated when a total of 35 mL of toluene was poured into the flask, and the color turned from white to transparent. After 60 hours, filtration gave 0.28 g of the filtered substance in a yield of 63%.

(ii) Synthesis of T3PyTRZ

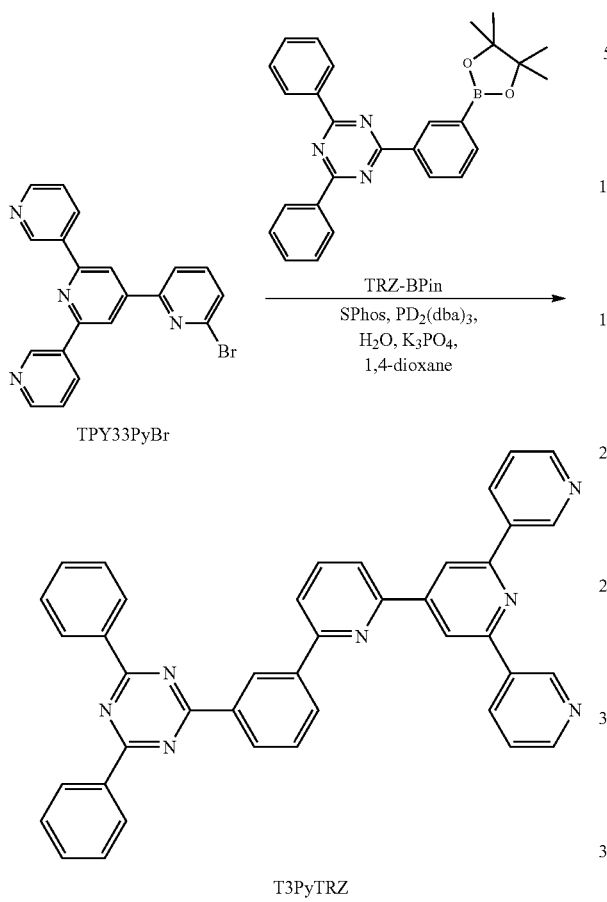

To a 100 mL four-necked flask, 0.78 g (2.0 mmol) of TPY33PyBr, 1.04 g (2.4 mmol) of TRZ-Bpin, 43 mL of 1,4-dioxane, 3.74 g of tripotassium phosphate and 13 mL of water were added in order, and the mixture was bubbled with nitrogen for 1 hour. After bubbling, 0.033 g of S-Phos and 0.037 g of Pd$_2$(dba)$_3$ were further added, and the mixture was heated to reflux at 104° C. At first, the mixture was transparent yellow but turned turbid yellow immediately after being stirred, and then it turned turbid orange. After 18 hours, a new spot of Rf-value 0.22 was observed and the reaction was stopped. The precipitate was filtered out and washed with water. The product was dispersed and washed in 100 mL of methanol to produce white solid T3PyTRZ.

The product was purified by silica gel column chromatography. Chloroform was used as eluent, and the polarity was gradually increased by adding methanol. The white solid T3PyTRZ (1.19 g, 97%) was obtained.

The product was recrystallized from toluene and ethanol. To a 500 mL round-bottom flask, 0.90 g of T3PyTRZ and 400 mL of 3:1 toluene to ethanol were added, and the mixture was stirred at approximately 100 to 110° C. using an oil bath to completely dissolve the T3PyTRZ. The flask equipped itself with a Dean-Stark trap, and the amount of solvent was reduced by degrees according to the principle of reflux. When the amount of solvent was reduced by half, that is, was reduced to 200 mL, the target compound was deposited in the solution. The heating and stirring was stopped, and 20 hours later, a white solid (698 mg, 77.6%) was collected by filtration and dried under reduced pressure.

The $^1$HNMR was carried out and the purity was determined by the ultra-performance liquid chromatography (UPLC). The results were shown below.

$^1$H-NMR (400 MHz, CDCl$_3$) δ 9.51-9.49 (m, 3H), 8.92 (d, J=8.2 Hz, 1H), 8.81 (d, J=7.8 Hz, 4H), 8.71-8.70 (m, 2H), 8.59-8.52 (m, 5H), 8.11-8.06 (m, 2H), 8.02-7.99 (m, 1H), 7.80 (t, J=7.8 Hz, 1H), 7.61 (t, J=7.3 Hz, 2H), 7.57-7.52 (m, 4H), 7.42 (dd, J=8.0, 4.8 Hz, 2H) ppm UPLC (retention time (min); peak area (%)) (0.63 min; 0.02%), (0.71 min; 0.09%), (0.83 min; 99.56%), (1.03 min; 0.33%)

[Example 6] Synthesis of T4PyTRZ (i) Synthesis of TPY44PyBr

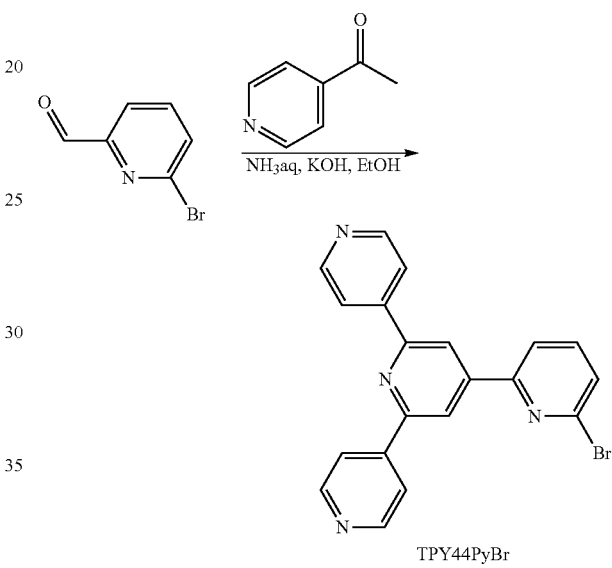

To a 500 mL Erlenmeyer flask, 5.0 g (26.9 mmol) of 6-bromo-2-pyridinecarboxaldehyde, 5.85 mL of 4-acetylpyridine, 136 mL of ammonia water, 201 mL of ethanol, and 1.5 g of potassium hydroxide were added in order, and the mixture was stirred. At first, the mixture was a transparent yellow solution, but turned transparent red immediately after being stirred, and then the solution turned turbid yellow. After the solution was stirred for 25 hours, TLC confirmed the disappearance of starting materials and a spot of Rf-value 0.25 corresponding to the target compound, and the reaction was stopped. The precipitate was filtered out and washed with ethanol. The pale yellow solid obtained was dispersed and washed in 100 mL of methanol to produce 2.89 g of white solid TPY44PyBr in a yield of 27%.

The product was recrystallized from toluene. To a 200 mL round-bottom flask, 3.68 g of TPY44PyBr and 30 mL of toluene were added, and the mixture was stirred at approximately 100 to 110° C. using an oil bath. Toluene was added by 5 mL to the flask until 110 mL. The solution became saturated when a total of 140 mL of toluene was poured into the flask, and the color turned from white to transparent. After 20 hours, 8.26 g of the precipitate mixed with some toluene was filtered out. The filtered substance was again recrystallized from toluene in the same way. After 60 hours, 1.95 g of the precipitate was filtered out in a yield of 53%.

(ii) Synthesis of T4PyTRZ

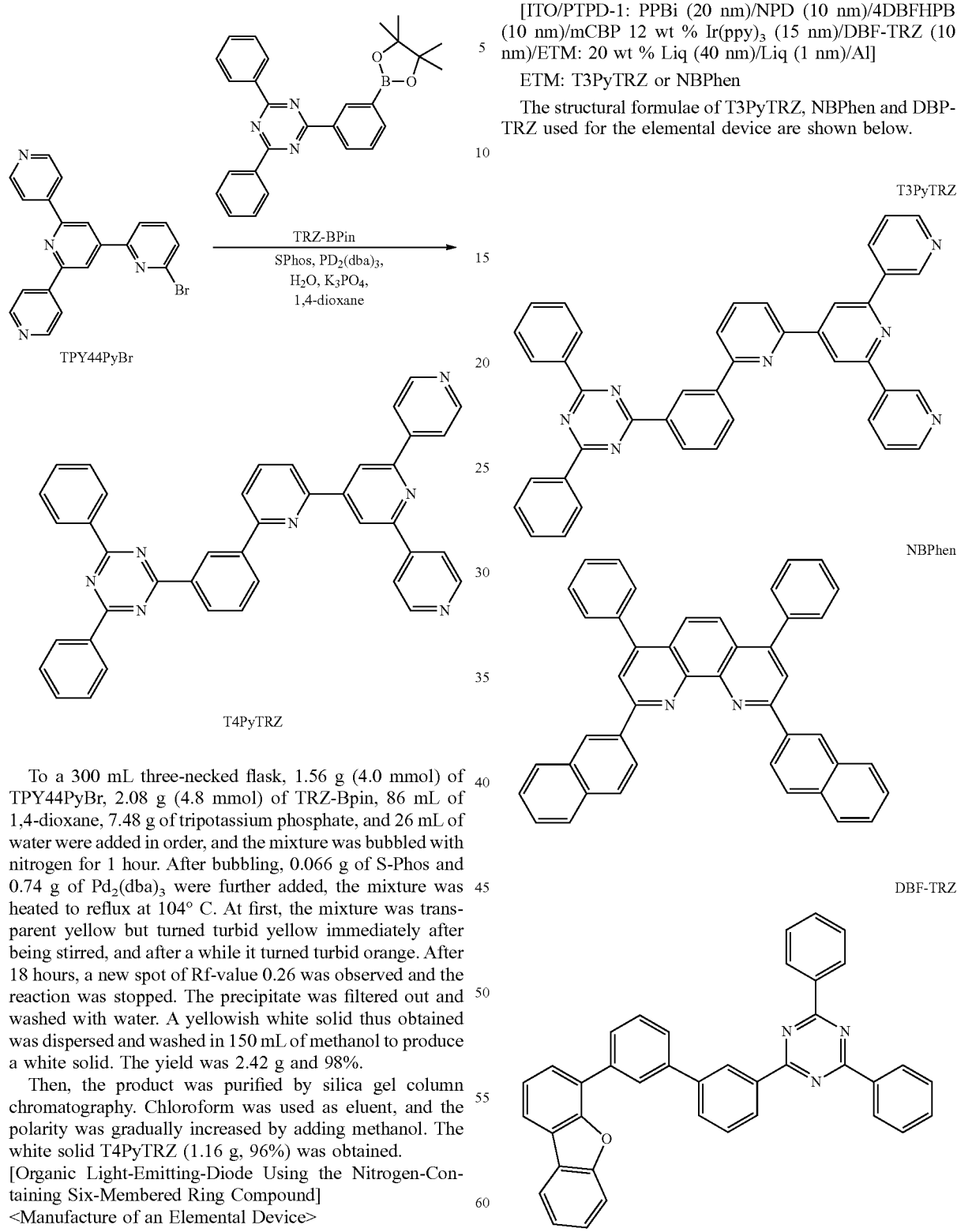

To a 300 mL three-necked flask, 1.56 g (4.0 mmol) of TPY44PyBr, 2.08 g (4.8 mmol) of TRZ-Bpin, 86 mL of 1,4-dioxane, 7.48 g of tripotassium phosphate, and 26 mL of water were added in order, and the mixture was bubbled with nitrogen for 1 hour. After bubbling, 0.066 g of S-Phos and 0.74 g of Pd$_2$(dba)$_3$ were further added, the mixture was heated to reflux at 104° C. At first, the mixture was transparent yellow but turned turbid yellow immediately after being stirred, and after a while it turned turbid orange. After 18 hours, a new spot of Rf-value 0.26 was observed and the reaction was stopped. The precipitate was filtered out and washed with water. A yellowish white solid thus obtained was dispersed and washed in 150 mL of methanol to produce a white solid. The yield was 2.42 g and 98%.

Then, the product was purified by silica gel column chromatography. Chloroform was used as eluent, and the polarity was gradually increased by adding methanol. The white solid T4PyTRZ (1.16 g, 96%) was obtained.

[Organic Light-Emitting-Diode Using the Nitrogen-Containing Six-Membered Ring Compound]

<Manufacture of an Elemental Device>

An elemental device was manufactured using NPD as a hole transport material, mCBP as a host material, and Ir(ppy)$_3$ as a phosphorescent dopant. NBPhen was used as a material for comparison. A large vacuum vapor depositing system was used for the film formation and the obtained film was evaluated.

The structure of the elemental device is shown below (FIG. 1). ETM represents an electron transport material.

[ITO/PTPD-1: PPBi (20 nm)/NPD (10 nm)/4DBFHPB (10 nm)/mCBP 12 wt % Ir(ppy)$_3$ (15 nm)/DBF-TRZ (10 nm)/ETM: 20 wt % Liq (40 nm)/Liq (1 nm)/Al]

ETM: T3PyTRZ or NBPhen

The structural formulae of T3PyTRZ, NBPhen and DBP-TRZ used for the elemental device are shown below.

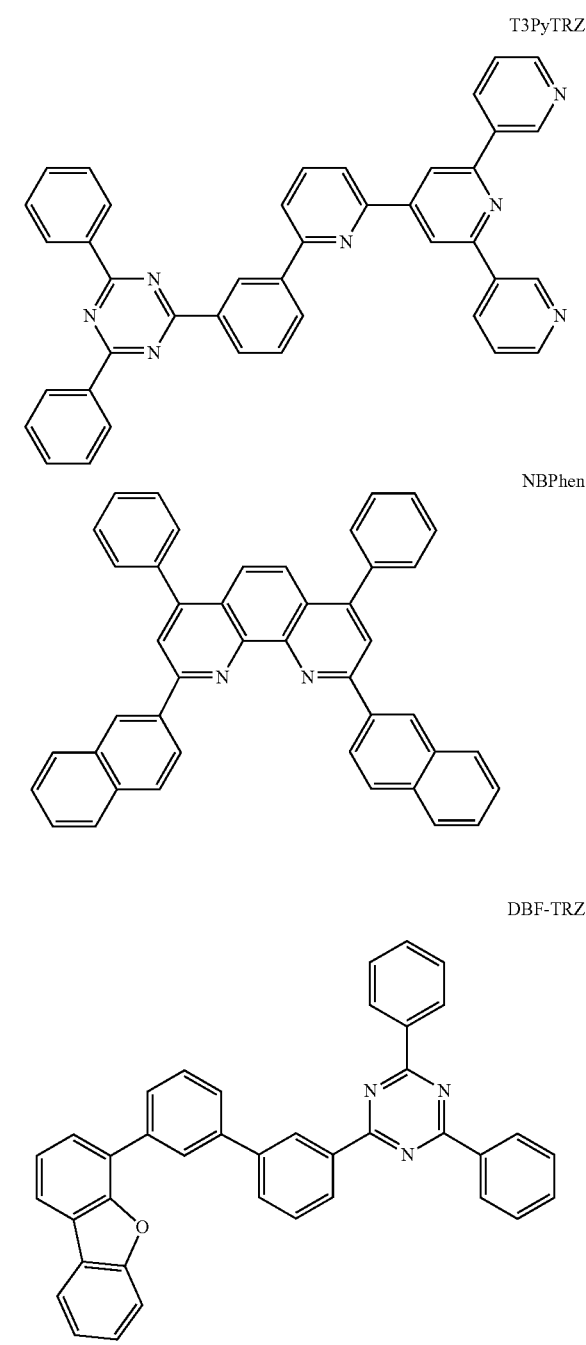

<Evaluation of an Elemental Device>

The evaluation results of the elemental device manufactured using the T3PyTRZ and NBPhen are shown in Table 4.

TABLE 4

| ETM | $V_{on}$[a] [V] | $V_{100}/\eta_{p,100}/\eta_{ext,100}$[b] [V, lm/W, %] | $V_{1000}/\eta_{p,1000}/\eta_{ext,1000}$[c] [V, lm/W, %] | $LT_{50}$[d] [h] |
|---|---|---|---|---|
| T3PyTRZ | 2.64 | 3.24/87.4/25.1 | 3.78/72.5/24.1 | 147 |
| NBphen | 2.68 | 3.24/79.7/23.2 | 3.77/55.6/18.6 | 111 |

[a] Voltage (V) at 1 cd/m².
[b] Voltage (V), power efficiency ($\eta_p$) and external quantum efficiency ($\eta_{ext}$) at 100 cd/m².
[c] Voltage (V), power efficiency ($\eta_p$) and external quantum efficiency ($\eta_{ext}$) at 1000 cd/m².
[d] Operational lifetime: 50% decay of initial luminance at current density of 25 mA/cm².

The driving voltage (1 cd/m²) of the elemental device manufactured using T3PyTRZ is equal to that of NBPhen. This is presumably because the deep LUMO level of T3PyTRZ facilitates more electron injection from the cathode. Commensurate driving voltages are also observed at 100 cd/m² and 1000 cd/m² which are the luminance practically required for smartphones and large-screen TVs. The present invention has accomplished 1.1 to 1.3 times higher power efficiency. The external quantum efficiency reaches nearly 25%, which shows that the roll-off is successfully reduced. The elemental device of the present invention is considered to attain high efficiency without losing good carrier balance.

What is claimed is:

1. A compound having a nitrogen-containing six-membered aromatic ring structure represented by the following general formula (5):

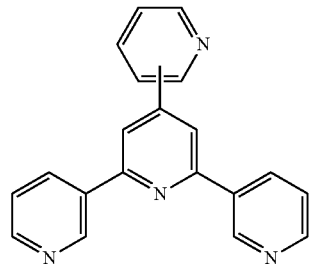

(5)

wherein in the general formula (5), all or part of hydrogen atoms constituting the nitrogen-containing six-membered aromatic structure are substituted by an aryl group having 6 to 16 core carbon atoms.

2. A compound having a nitrogen-containing six-membered aromatic ring structure represented by the following formula (6):

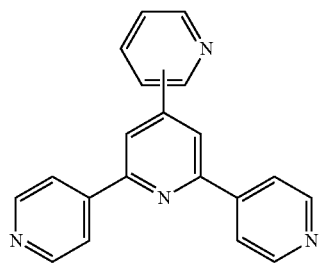

(6)

wherein in the general formula (6), all or part of hydrogen atoms constituting the nitrogen-containing six-membered aromatic ring structure are substituted by an aryl group having 10 to 18 core carbon atoms.

3. A compound having a nitrogen-containing six-membered aromatic ring structure represented by the following general formula (6):

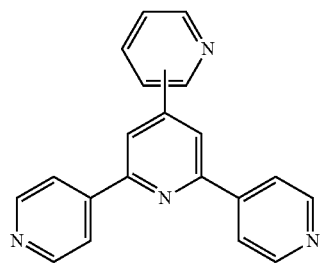

(6)

wherein in the general formula (6), all or part of hydrogen atoms constituting only one of four pyridine rings are substituted by an aryl group having 6 to 18 core carbon atoms.

4. A compound having a nitrogen-containing six-membered aromatic ring structure represented by one selected from the group consisting of:

s3PyTPy

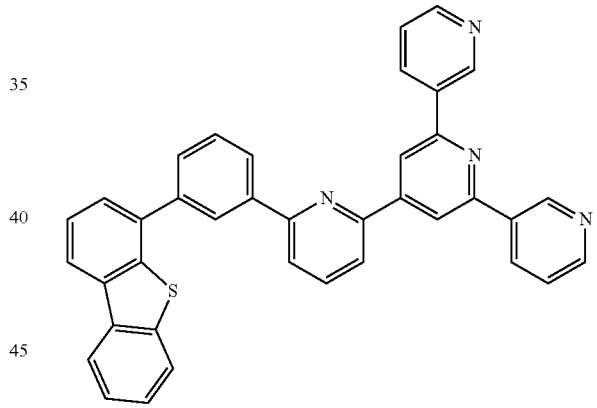

s4PyTPy

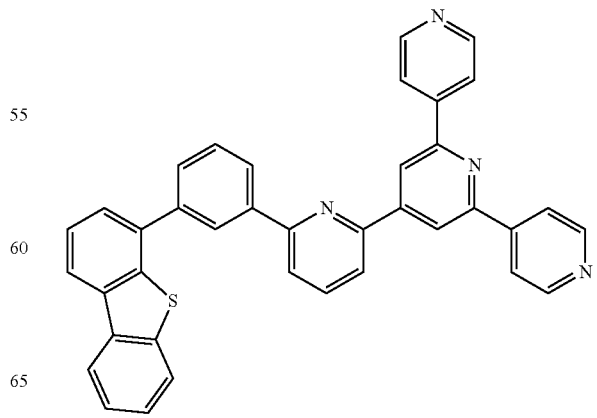

ss3PyTPy
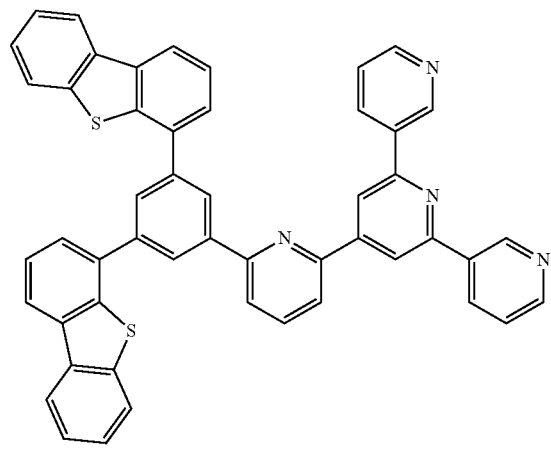
8d3PyTPy
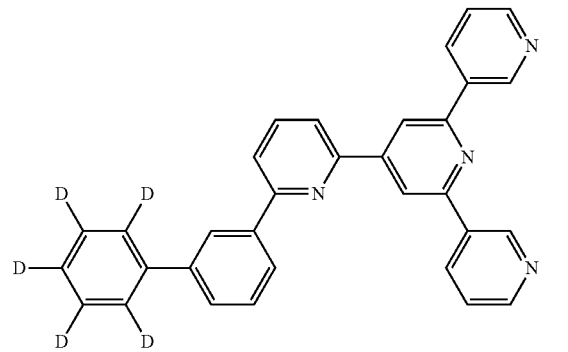
8d4PyTPy
TRZ3PyTPy
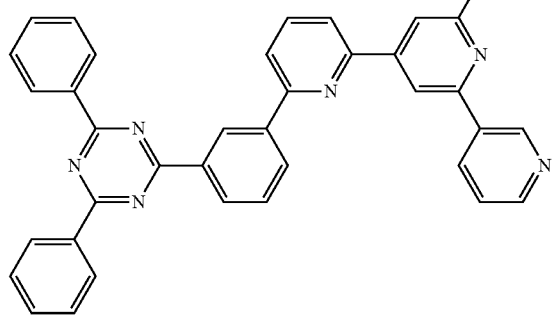
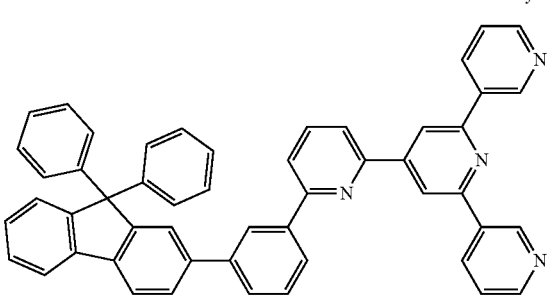
DPF3PyTPy
TRZ4PyTPy
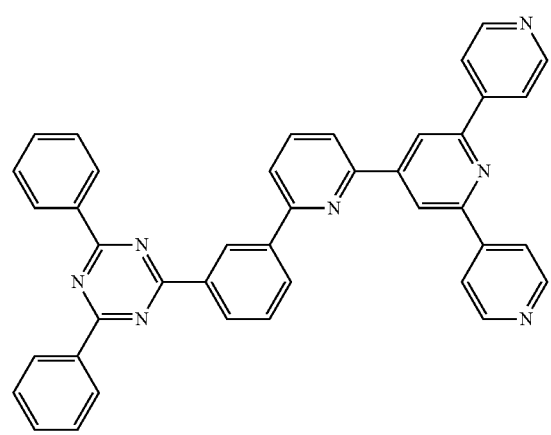
DPF4PyTPy
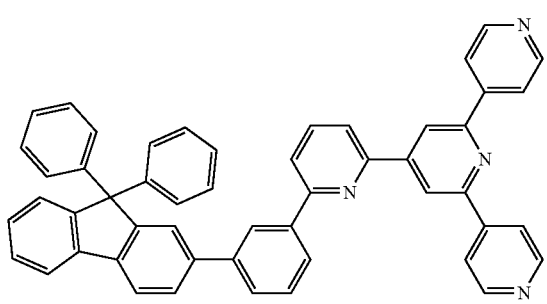

-continued
TP3PyTPy
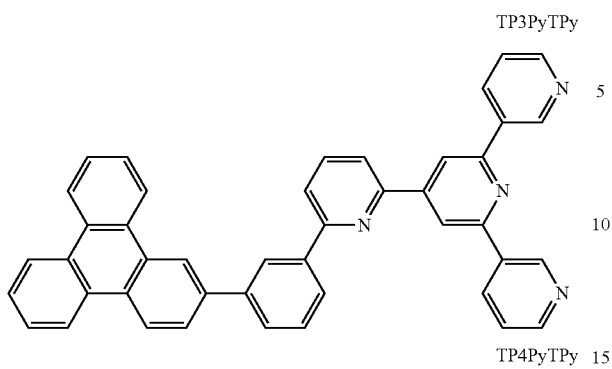
TP4PyTPy
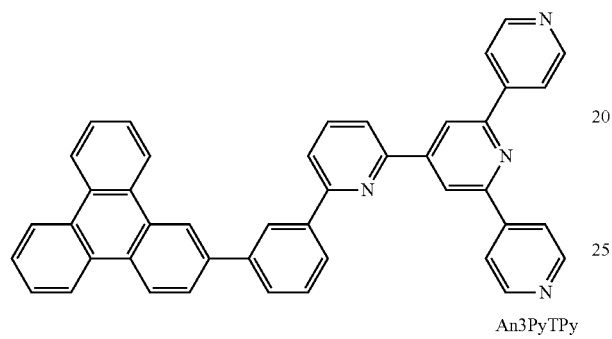
An3PyTPy
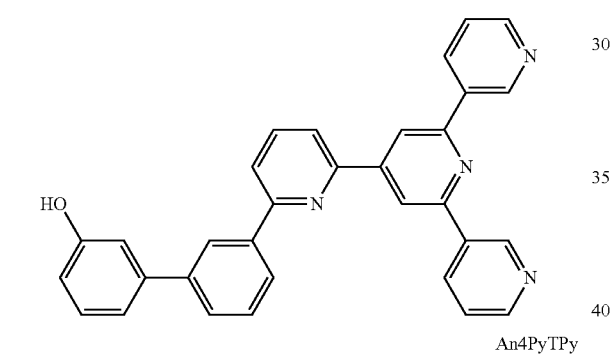
An4PyTPy
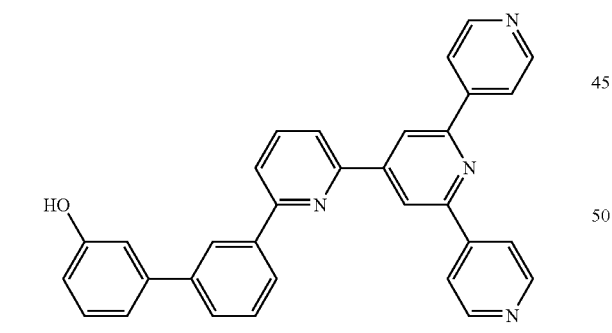
SBF3PyTPy
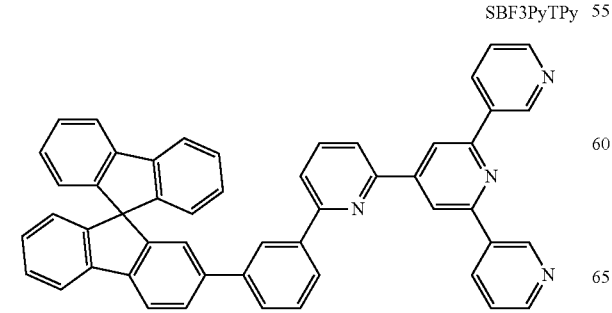
-continued
SBF4PyTPy
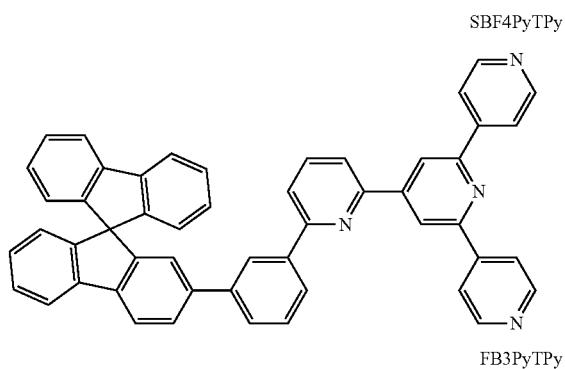
FB3PyTPy
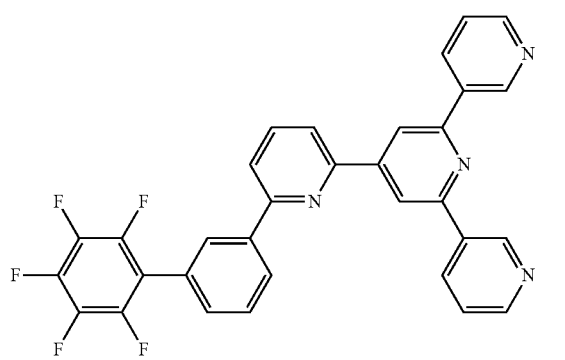
FB4PyTPy
9PhCz3PyTPy
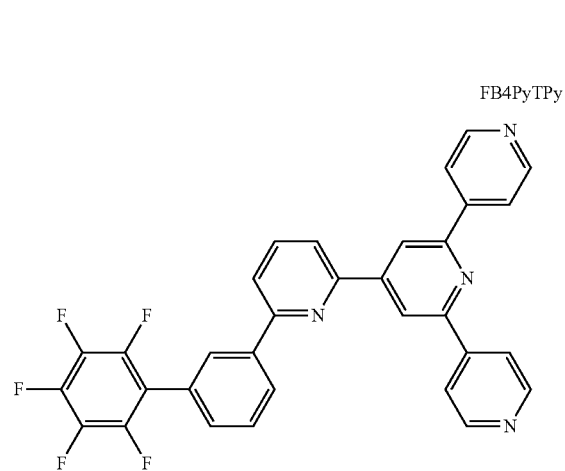

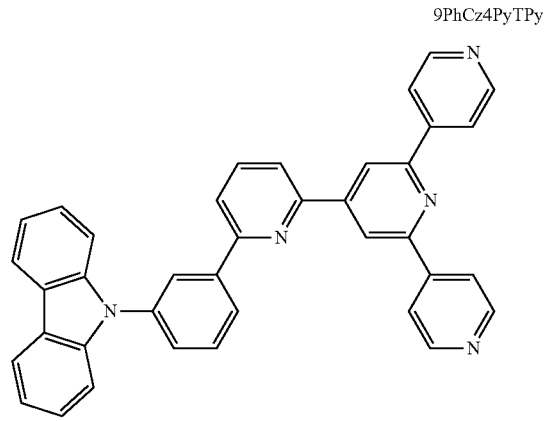
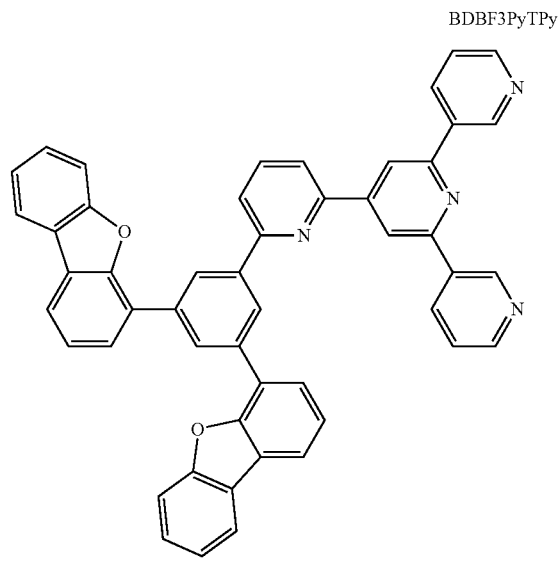

-continued

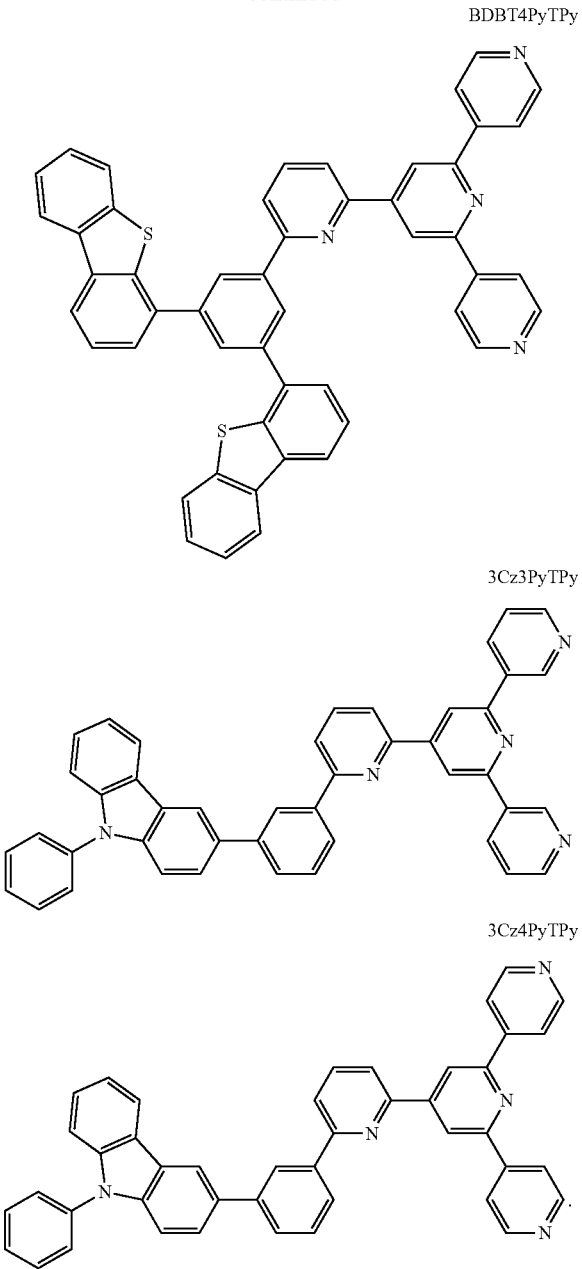

5. A material for organic light-emitting-diode comprising the compound having the nitrogen-containing six-membered aromatic ring structure according to claim 3.

6. An electron transport material for organic light-emitting-diode comprising the compound having the nitrogen-containing six-membered aromatic ring structure according to claim 1.

7. An organic light-emitting-diode having a pair of anode and cathode electrodes and at least one organic layer including a light-emitting layer between the pair of the electrodes, wherein any of the organic layers between the light-emitting layer and the cathode comprises the compound having the nitrogen-containing six-membered aromatic ring structure according to claim 1.

8. A material for organic light-emitting-diode comprising the compound having the nitrogen-containing six-membered aromatic ring structure according to claim 2.

9. An electron transport material for organic light-emitting-diode comprising the compound having the nitrogen-containing six-membered aromatic ring structure according to claim 2.

10. A material for organic light-emitting-diode comprising the compound having the nitrogen-containing six-membered aromatic ring structure according to claim 3.

11. An electron transport material for organic light-emitting-diode comprising the compound having the nitrogen-containing six-membered aromatic ring structure according to claim 3.

12. An organic light-emitting-diode having a pair of anode and cathode electrodes and at least one organic layer including a light-emitting layer between the pair of the electrodes, wherein any of the organic layers between the light-emitting layer and the cathode comprises the compound having the nitrogen-containing six-membered aromatic ring structure according to claim 2.

13. An organic light-emitting-diode having a pair of anode and cathode electrodes and at least one organic layer including a light-emitting layer between the pair of the electrodes, wherein any of the organic layers between the light-emitting layer and the cathode comprises the compound having the nitrogen-containing six-membered aromatic ring structure according to claim 3.

14. A material for organic light-emitting-diode comprising the compound having the nitrogen-containing six-membered aromatic ring structure according to claim 4.

15. An electron transport material for organic light-emitting-diode comprising the compound having the nitrogen-containing six-membered aromatic ring structure according to claim 4.

16. An organic light-emitting-diode having a pair of anode and cathode electrodes and at least one organic layer including a light-emitting layer between the pair of the electrodes, wherein any of the organic layers between the light-emitting layer and the cathode comprises the compound having the nitrogen-containing six-membered aromatic ring structure according to claim 4.

* * * * *